US005804436A

United States Patent [19]
Okun et al.

[11] Patent Number: 5,804,436
[45] Date of Patent: Sep. 8, 1998

[54] APPARATUS AND METHOD FOR REAL-TIME MEASUREMENT OF CELLULAR RESPONSE

[75] Inventors: Ilya Okun; Alex Okun, both of San Diego, Calif.

[73] Assignee: Axiom Biotechnologies, Inc., San Diego, Calif.

[21] Appl. No.: 691,356

[22] Filed: Aug. 2, 1996

[51] Int. Cl.$^6$ .................................................... C12M 3/00
[52] U.S. Cl. .................................. 435/286.1; 435/286.4; 435/286.5; 435/287.1; 435/287.3; 422/82.05
[58] Field of Search ............................. 435/283.1, 286.1, 435/286.4, 286.5, 286.7, 287.1, 287.3, 288.7; 422/81, 82.05; 436/63, 79, 172

[56] References Cited

U.S. PATENT DOCUMENTS

| | | | |
|---|---|---|---|
| 3,772,154 | 11/1973 | Isenberg et al. | 195/103.5 R |
| 3,826,899 | 7/1974 | Ehrlich et al. | 235/92 PC |
| 4,271,123 | 6/1981 | Curry et al. | 422/64 |
| 4,343,782 | 8/1982 | Shapiro | 424/3 |
| 4,632,808 | 12/1986 | Yamamoto et al. | 422/72 |
| 4,676,951 | 6/1987 | Armes et al. | 422/65 |
| 4,678,752 | 7/1987 | Thorne et al. | 435/291 |
| 4,766,078 | 8/1988 | Gang | 435/291 |
| 5,278,048 | 1/1994 | Parce et al. | 436/29 |
| 5,320,808 | 6/1994 | Holen et al. | 422/64 |
| 5,401,629 | 3/1995 | Harpold et al. | 435/6 |
| 5,436,128 | 7/1995 | Harpold et al. | 435/6 |
| 5,463,564 | 10/1995 | Agrafiotis et al. | 364/496 |
| 5,541,061 | 7/1996 | Fodor et al. | 435/6 |
| 5,556,762 | 9/1996 | Pinilla et al. | 435/7.21 |
| 5,559,002 | 9/1996 | Uzan et al. | 435/7.9 |
| 5,569,588 | 10/1996 | Ashby et al. | 435/6 |
| 5,573,909 | 11/1996 | Singer et al. | 435/6 |
| 5,574,656 | 11/1996 | Agrafiotis et al. | 364/500 |
| 5,585,275 | 12/1996 | Hudson et al. | 436/518 |
| 5,601,992 | 2/1997 | Lerner et al. | 435/7.2 |
| 5,620,894 | 4/1997 | Barger et al. | 435/286.2 |
| 5,630,706 | 5/1997 | Yang | 417/3 |

FOREIGN PATENT DOCUMENTS

| | | | |
|---|---|---|---|
| WO 90 04645 | 5/1990 | WIPO | C12Q 1/02 |
| WO 93 13423 | 7/1993 | WIPO | G01N 35/02 |
| WO 96 30760 | 10/1996 | WIPO | G01N 33/50 |

OTHER PUBLICATIONS

"Cytosensor® Microphysiometer at Work Reference Guide," Molecular Devices Corporation, 1994.

"The Cytosensor Microphysiometer: Biological Applications of Silicon Technology," McConnell, et al., *Science*, vol. 257, pp. 1906–1912, 25 Sep. 1992.

"Evaluting Receptor Desensitization using the Cytosensor® Microphysiometer System," Molecular Devices Corporation, prior to Aug. 1996.

"Cytosensor™ Microphysiometer," ad Molecular Devices Corporation, prior to Aug. 1996.

"Real–Time Measurements of Receptor Activity: Applications of Microphysiometric Techniques to Receptor Biology," Salon, J. and Owicki, J., *Methods in Neurosciences*, vol. 25, pp. 201–224, 1995.

"Some Quantitative Uses of Drug Antagonist," Arunlakshana, O. & Schild, H.O., *Brit. J. Pharmacol.*, vol. 14, pp. 48–58, 1959.

(List continued on next page.)

*Primary Examiner*—David A. Redding
*Attorney, Agent, or Firm*—Knobbe, Martens, Olson & Bear LLP

[57] ABSTRACT

An apparatus and method for real-time measurement of a cellular response of a test compound or series of test compounds on a flowing suspension of cells in which a homogeneous suspension of living cells is combined with a concentration of a test compound, directed through a detection zone, and a cellular response of the living cells is measured in real time as the cells in the test mixture are flowing through the detection zone. The apparatus may be used in automated screening of libraries of compounds, and is capable of real-time variation of concentrations of test and standard compounds and generation of dose/response profiles within a short timespan.

50 Claims, 26 Drawing Sheets

OTHER PUBLICATIONS

"Inositol Phosphate and Cell Signaling," Berridge, et al., *Nature*, vol. 341, pp. 197–205, 1989.

"Inositol Triphosphate and Calcium Signaling," Berridge, M.J., *Nature*, vol. 361, pp. 315–325, 1993.

"Relationship Between the Inhibition Constant ($K_i$) and the Concentration of the Inhibitor Which Causes 50 Percent Inhibition ($IC_{50}$) of an Enzymatic Reaction," Cheng, et al., *Biochem. Pharmacol.*, vol. 22, pp. 3099–3108, 1973.

"Calcium Signaling," Clapham, D.E., *Cell*, vol. 80, pp. 259–268, 1995.

"Genetic Reconstitution of Functional Acetylcholine Receptor Channels in Mouse Fibroblasts," Claudio, et al., *Science*, vol. 239, pp. 1688–1694, 1987.

"Phospholipid Signaling," Divecha, et al., *Cell*, vol. 80, pp. 269–278, 1995.

"Biospecific Interaction Analysis Using Surface Plasmon Resonance Detection Applied to Kinetic, Binding Site and Concentration Analysis," Fagerstam, et al., *Journal of Chromatography*, vol. 597, pp. 397–410, 1992.

"Theories of Drug Antagonism," Gaddum, J.H., *Pharmacol. Rev.*, vol. 9, pp. 211–218, 1957.

"A new generation of $Ca^{2+}$ Indicators With Greatly Improved Fluorescent Properties," Grynkiewicz, et al., *J. Biol. Chem.*, vol. 260, pp. 3440–3450, 1985.

"MAP Kinase Pathways in Yeast: For Mating and More," Herskowitz, I., *Cell*, vol. 80, pp. 187–197, 1995.

"Transcriptional Regulation by Extracellular Signals: Mechanisms and Specificity," Hill, et al., *Cell*, vol. 80, pp. 199–211, 1995.

"Estimation of Antagonist $K_b$ From Inhibition Curves in Functional Experiments: Alternatives to the Cheng–Prusoff Equation," Lazareno, et al., *TIPS*, vol. 14, pp. 237–239, 1993.

"Specificity of Receptor Tyrosine Signaling: Transient Versus Sustained Extracellular Signal Regulated Kinase Activation," Marshall, C.J., *Cell*, vol. 80, pp. 179–185, 1995.

"Calcium, Calmodulin and Cell Cycle Regulation," Means, A.R., *FEBS Lett.*, vol. 347, pp. 1–4, 1994.

"Nuclear Calcium Transport and the Role of Calcium in Apoptosis," Nicotera, et al., *Cell Calcium*, vol. 16, pp. 279–288, 1994.

"Pseudo–Noncompetitive Antagonism by BQ–123 of Intracellular Calcium transients Mediated by Human $ET_A$ Endothelin Receptor," Sakamoto, et al, *Biochem. Biophys. Res. Comm.*, vol. 200, pp. 679–686, 1994.

"CREB a $Ca^{2+}$–Regulated Transcription Factor Phosphorylated by Calmodulin–Dependent Kinases," Sheng, et al., *Science*, vol. 252, pp. 1427–1430, 1991.

"Regulation of Phospholipase C by G Proteins," Sternweis, et al., *Trends Biol. Sci.*, vol. 17, pp. 502–506, 1992.

"Does a Radiolabeled Ligand Bind to a Homogenous Population of Non–Interacting Receptor Sites?" Swillens, et al., *TiPS*, vol. 16, pp. 151–155, 1995.

"Quantitative Analysis of Drug–receptor Interactions: 1. Determination of Kinetic and Equilibrium Properties," Weiland, et al., *Life Sciences*, vol. 29, pp. 313–330, 1981.

| | PRIMING VALVES | | | | DIVERTING VALVES | | | PROPORTIONING VALVES | |
|---|---|---|---|---|---|---|---|---|---|
| STEP | 345 | 341 | 313 | 329 | 335 | 333 | 347 | 327 | 311 |
| START | − | − | − | − | − | − | − | − | − |
| 608 | + | | + | | | | | | |
| 612 | | | | | | | | + | |
| 614 | | | | | | | | − | |
| 616 | | | − | | | | | | |
| 618 | | | | + | | | | | |
| 620 | | | | | | | | | + |
| 622 | | | | | | | | | − |
| 624 | | | | − | | | | | |
| 626 | | | | | + | + | | | |
| 628 | | | | | − | | | | |
| 630 | | | | | | − | | | |
| 632 | − | + | | | | | | | |
| 636 | | | | | | | + | | |
| 638 | | − | | | | | − | | |
| STOP | − | − | − | − | − | − | − | − | − |

FIG. 6d

| FIG. 7a |
|---|
| FIG. 7b |
| FIG. 7c |
| FIG. 7d |
| FIG. 7e |
| FIG. 7f |
| FIG. 7g |

FIG. 7

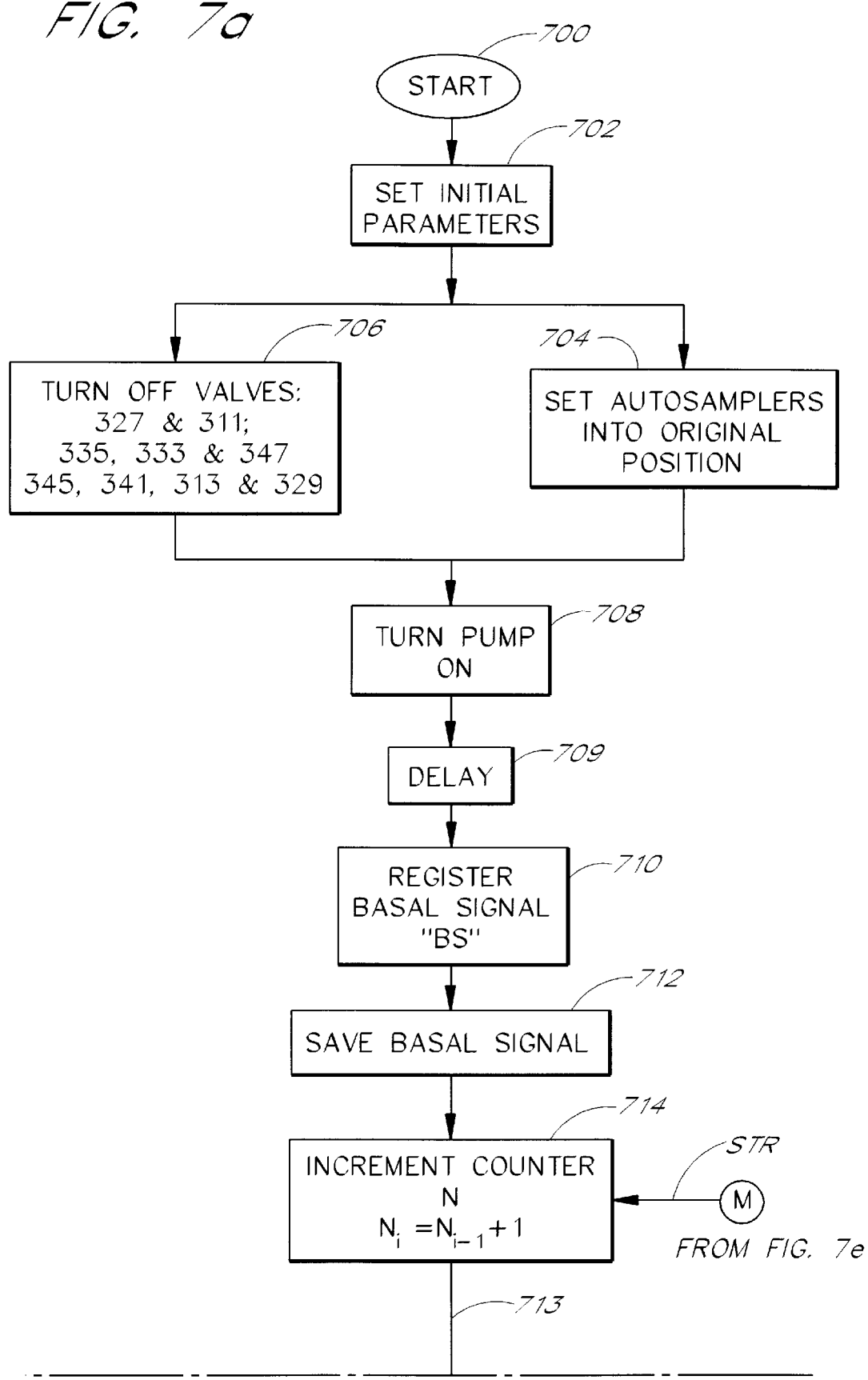

| FIG. 8a |
|---|
| FIG. 8b |
| FIG. 8c |
| FIG. 8d |
| FIG. 8e |

FIG. 8

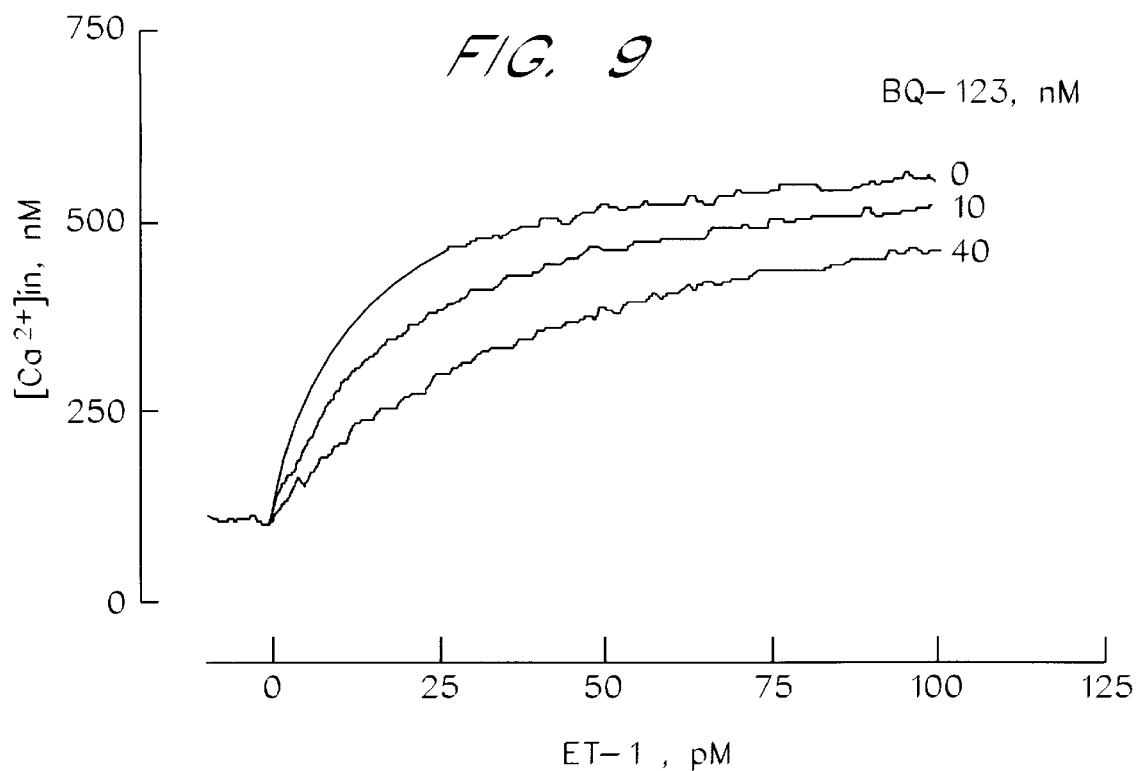
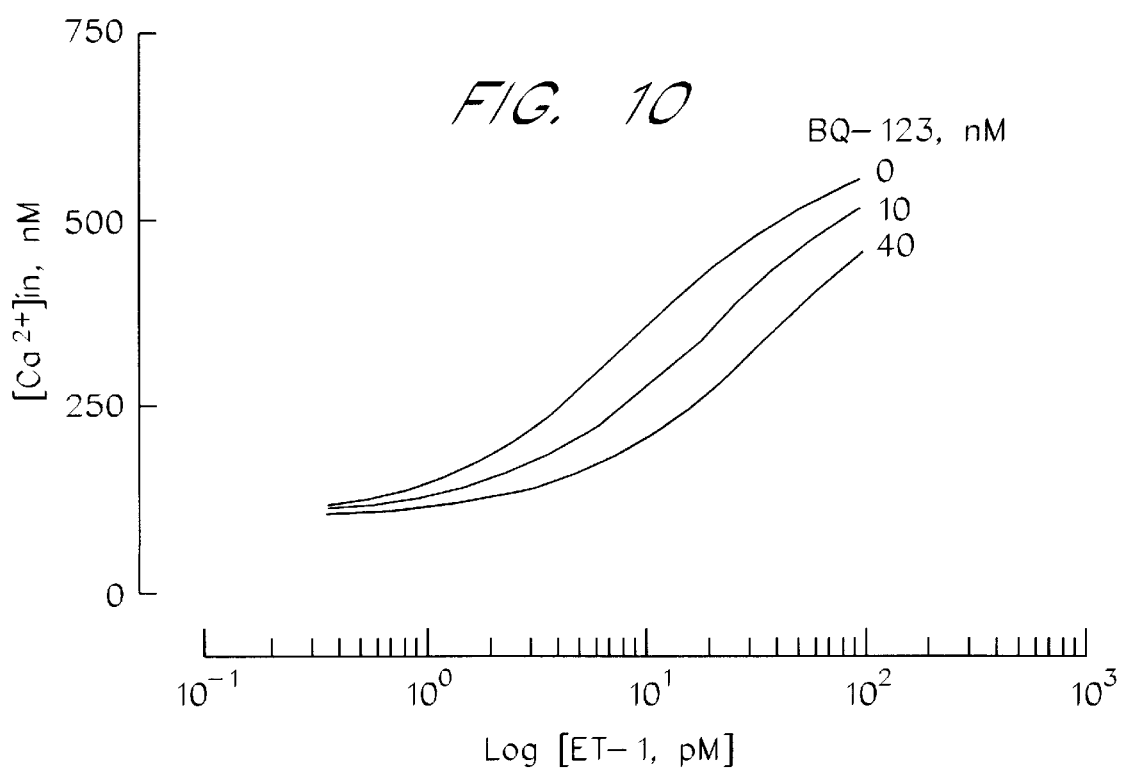

APPARATUS AND METHOD FOR REAL-TIME MEASUREMENT OF CELLULAR RESPONSE

FIELD OF THE INVENTION

This invention relates generally to an apparatus for screening and the pharmacological profiling of compounds modulating a cellular physiological response. This invention also relates to devices for rapid assessment of the properties of compounds that modulate the activities of cell surface receptors and ion channels. More specifically, this invention relates to methods and apparatus for detecting, evaluating and characterizing the ability and potency of substances to act as agonists or antagonists against receptors and ion channels localized on a cell surface membrane.

BACKGROUND INFORMATION

Biological cells contain receptor molecules located on their external membrane. The function of these receptors is to "sense" the cell environment and supply the cell with an input signal about any changes in the environment. In eukaryotic organisms such cell environment is comprised of the neighboring cells and the function of the receptor is to allow cells to communicate with each other directly (the paracrine regulatory system) or indirectly (the endocrine regulatory system) thus achieving harmonized response of a tissue, organ or a whole organism. In prokaryotic cells, the surface localized receptors provide a means for detecting extracellular environment.

Having received such a signal, neurotransmitters, hormones, chemoattractant or chemorepellant substances for example, the surface localized receptors transmit this information about extracellular environment into the cell through specific intracellular pathways in such a way that the cell responds in the specific fashion to accommodate these changes. When there is an altered supply of the external signal molecules or an altered activity of the cell surface molecules, the cell response would be abnormal causing malfunctioning of a tissue or an organ.

In eucariotic; cells, receptor molecules determine the selective response of the cell. Each type of receptor can interact only with a specific set of ligand molecules. For example, adrenergic receptors interact with adrenaline and noradrenaline, cholinergic receptors interact with acetylcholine, serotoninergic receptors interact with 5-hydroxytriptamine, dopamineergic with DOPA and so on. The cells derived from the different tissues invariably express specific sets of tissue receptors. Different types of receptors are connected to different signal transduction pathways. For example, nicotinic cholinergic receptor, upon binding acetylcholine molecule, directly activates sodium channel (Claudio et al., 1987, is incorporated herein by reference). G-protein coupled receptors activate enzymes of second messenger pathways, for example, adenylate cyclase or phospholipase C with subsequent activation of cAMP or phosphoinositide cascades (Divecha and Itvine, 1995, is incorporated herein by reference). Receptor tyrosine kinases activate cascade of MEK/MAPK kinases leading to cell differentiation and proliferation (Marshall, 1995 and Herskowitz, 1995, are incorporated herein by reference)]. Cytokine receptors activate JAK/STAT cascade which in turn can regulate other pathways as well as activate gene transcription (Hill & Treisman, 1995, is incorporated herein by reference).

Together with the receptors, the cell surface membrane carries ion pumps, ion transporters and ion channels. These molecular assemblies work in concert to maintain intracellular ion homeostasis. Any changes in the activity of these systems would cause a shift in the intracellular concentrations of ions and consequently to the cell metabolic response.

Ion pumps act to maintain transmembrane ion gradients utilizing ATP as a source of energy. The examples of the ion pumps are: $Na^+/K^+$-ATPase maintaining transmembrane gradient of sodium and potassium ions, $Ca^{2+}$-ATPase maintaining transmembrane gradient of calcium ions and $H^+$-ATPase maintaining transmembrane gradient of protons.

Ion transporters use the electrochemical energy of transmembrane gradients of one ion species to maintain gradients of other ion counterpart. For example, the $Na^+/Ca^{2+}$-exchanger uses the chemical potential of the sodium gradient directed inward to pump out calcium ions against their chemical potential.

Ion channels, upon activation, allow for the ions to move across the cell membrane in accordance with their electrochemical potential. There are two main types of ion channels: voltage operated and ligand-gated. Voltage operated channels are activated to the open state upon changes in transmembrane electric potential. Sodium channels in the neuronal axon or L-type calcium channels in neuromuscular junctions exemplify this kind of channel. Ligand-gated channels are activated to the open state upon binding a certain ligand with the chemoreceptor part of their molecules. The classical example of ligand-gated channels is nicotinic cholinergic receptor which, at the same time, is the sodium channel.

There are numerous methods for detecting ligand/receptor interaction. The most conventional are methods where the affinity of a receptor to a substance of interest is measured in radioligand binding assays. In these assays, one measures specific binding of a reference radiolabeled ligand molecule in the presence and in the absence of different concentrations of the compound of interest. The characteristic inhibition parameter of the specific binding of the reference radiolabeled ligand with the compound of interest, $IC_{50}$, is taken as a measure of the affinity of the receptor to this compound (Weiland & Molinoff, 1981 and Swillens et all., 1995, are incorporated herein by reference). Recent advances in microchip sensor technology made it possible to measure direct interactions of a receptor molecule with a compound of interest in real time. This method allows for determination of both association and dissociation rate constants with subsequent calculation of the affinity parameter (F__gerstam et al., 1992, is incorporated herein by reference). While being very precise and convenient, these methods do not allow to distinguish between agonist and antagonist activity of the compound.

The type of biological activity of the compounds, agonist or antagonist, may be determined in the cell based assays. In the methods described in Harpold & Brust, 1995, which is incorporated herein by reference, cells cotransfected with a receptor gene and reporter gene construct, are used to provide means for identification of agonist and antagonist potential pharmaceutical compounds. These methods are inconvenient because they require very laborious manipulations with gene transfection procedures, are highly time consuming and use artificially modified cells. Besides, to prove that the agonistic effect of a particular compound is connected to the stimulation of a transfected receptor, several control experiments with a positive and negative control cell lines should be performed as well.

Most closely related to the methods of this invention are the methods described in Parce et al., 1994, which is incorporated herein by reference. These prior art methods use natural cells and are based on registering the natural cell responses, such as the rate of metabolic acidification, to the biologically active compounds. The disadvantage of the prior art is low throughput speed, each measurement point taking about three minutes. Another disadvantage of the prior art is the use of cells immobilized on the internal surface of the measuring microflow chamber. This leads to the necessity of using separate silicon sensors, or cover slips, with the cells adherent to them for each concentration point of the agonist or antagonist, for the receptors that undergo desensitization upon binding to the agonist molecule. This results in high variability of the experimental results.

Ionized calcium, unlike other intracellular ion events, e.g. changes in the intracellular concentrations of protons, sodium, magnesium, or potassium, serves as the most common element in different signal transduction pathways of the cells ranging from bacteria to specialized neurons (Clapham, 1995, is incorporated herein by reference). There are two major pools which supply signal transduction pathways in the cell with the calcium ions, extracellular space and the endoplasmic reticulum. There are several mechanisms to introduce small bursts of calcium into cytosol for signal transduction.

Both excitable and nonexcitable cells have on their plasma membrane predominantly two receptor classes, G-protein coupled serpentine receptors (GPCSR) and the receptor tyrosine kinases (RTK), that control calcium entry into cell cytoplasm. Both GPCSR and RTK receptors activate phospholipase C to convert phosphatidylinositol into inositol(1,4,5)-trisphosphate (InsP$_3$) and diacylglicerol. InsP$_3$ acts as an intracellular second messenger and activates specialized receptor that spans the endoplasmic reticular membrane. The activation of this receptor triggers release of calcium ions from the endoplasmic reticulum (Berridge, 1993, is incorporated herein by reference). The calcium ions can also enter the cytoplasm of excitable and nonexcitable cell from extracellular environment through specialized voltageindependent $Ca^{2+}$- selective channels triggered by specific ligands. In nonexcitable cells, hyperpolarization of the plasma cell membrane also enhances entry of calcium ions through passive transmembrane diffusion along the electric potential. For example, opening of potassium channels brings the membrane potential to more negative values inside the cell, thus facilitating $Ca^{2+}$ entry across the plasma membrane. Excitable cells contain voltage-dependent $Ca^{2+}$ channels on their plasma membrane, which, upon membrane depolarization, open for a short period of time and allow inflow of $Ca^{2+}$ from external media into cytoplasm. The endoplasmic reticulum membrane as well as plasma membrane of the excitable cells contains InsP$_3$ receptors and $Ca^{2+}$- sensitive ryanodine receptors (RyR) releasing $Ca^{2+}$ from intracellular stores upon membrane receptor triggered phospholipase C activation or depolarization-induced short burst of $Ca^{2+}$ entry into cell cytoplasm from extracellular media respectively.

It is well established that G-protein coupled serpentine receptors initiate $Ca^{2+}$ mobilization through the activation of phospholipase C$_\beta$ (Sternweis and Smrcka, 1992, is incorporated herein by reference) whereas tyrosine kinase receptors activate phospholipase C$_\gamma$ with subsequent intracellular $Ca^{2+}$ mobilization (Berridge & Irvine, 1989, is incorporated herein by reference).

There are many plasma membrane G-protein coupled serpentine receptors, tyrosine kinase growth factor receptors and voltage- and ligand-regulated channels known to initiate intracellular $Ca^{2+}$ mobilization.

$Ca^{2+}$ plays an essential role in many functional processes of a cell. For example, $Ca^{2+}$ affects the cell cycle (Means, 1994, is incorporated herein by reference) and activates specific transcription factors (Sheng et al., 1991, is incorporated herein by reference). Scores of receptors and ion channels use the $Ca^{2+}$ signal to initiate events as basic as cell motility, contraction, secretion, division etc..

Increases in cytosolic and, consequently, in nuclear concentration of the $Ca^{2+}$ can also be a cell death promoting signal. For example, prolonged increase in free $Ca^{2+}$ activates degradation processes in programmed cell death, apoptosis, activates nucleases that cleave DNA and degrade cell chromatin, promotes DNA digestion by direct stimulation of endonucleases, or indirectly by activation of $Ca^{2+}$-dependent proteases, phosphatases and phospholipases, resulting in a loss of chromatin structural integrity (Nicotera et all., 1994, is incorporated herein by reference).

A development of intracellular fluorescent calcium indicators (Grynkiewicz et all., 1985, is incorporated herein by reference) made it possible for intracellular concentration of free calcium to be measured directly in the living cell. Thus the ability to register changes in intracellular calcium concentration provide the means for monitoring effects of different compounds useful in treating various diseases, whose action is thought to be a result of an interaction with membrane receptors and ion channels.

With the advent of combinatorial chemistry approaches to identify pharmacologically useful compounds, it is increasingly evident that there is a need for methods and apparatuses capable of performing automated characterization of pharmacological profiles and corresponding potencies of the compounds in synthesized combinatorial libraries. This would enable the rapid screening of a large number of compounds in the combinatorial library the identification of those compounds which have biological activity, and the characterization of those compounds in terms of potency, affinity and selectivity.

It is an object of this invention to provide methods for screening and the quantitative characterization of potentially pharmacologically effective compounds that specifically interact with and modulate the activity of cell membrane receptors, ion pumps and ion channels using living cells.

It is an additional object of this invention to provide methods capable of characterizing an affinity of the active compounds to the binding sites of the cell.

It is another additional object of this invention to provide methods to distinguish between agonistic and antagonistic activity of the compounds.

It is yet another additional object of this invention to provide methods to determine the nature of the receptor, ion channel or ion pump entity which is sensitive to the active compounds discovered during the screening process.

It is yet another additional object of this invention to provide methods to characterize cell receptor pattern for particular cell source tissue.

It is a specific object of this invention to provide an apparatus for fulfillment of the objectives above.

SUMMARY OF THE INVENTION

The present invention addresses the above and other needs by providing a method and corresponding apparatuses which allows the automated characterization of pharmacological profiles and corresponding potencies of compounds in synthesized combinatorial libraries. This enables the rapid screening of a large number of compounds in the combinatorial library, the identification of those compounds which have biological activity, and the characterization of those compounds in terms of potency, affinity and selectivity.

A variety of effects caused by the compounds to be screened may be detected and quantitatively characterized according to the present invention. Preferably, these effects include but are not limited to changes in intracellular concentration of ionized calcium, cAMP or pH, transmembrane potential and other physiological and biochemical characteristics of living cell which can be measured by a variety of conventional means, for example using specific fluorescent, luminescent or color developing dyes.

The present invention also includes methods of screening for agonist or antagonist activity of drugs, methods of characterizing their potency profiles, methods of identifying the receptor expression pattern of cell membrane ("receptor fingerprinting") and methods of determining toxicity profiles for the compounds. In these methods, a steady flow of cells is mixed with flows of the compound and a standard substance. The effects of the compound alone and in mixture with the standard substance are measured and provide the means for pharmacological profiling of the compounds, drug screening and cell receptor pattern characterizing.

In a preferred embodiment of the invention, the compounds to be screened and standard agonist and antagonist substances are organized in a 96-well plate format, or other regular two dimensional array, such as a 48-well and 24-well plate format or an array of test tubes. In another preferred embodiment of the invention, the non-adherent cells are grown in a suspension of freely flowing cells by growing them in an appropriate cell cultivating system.

In another preferred embodiment of the invention, the naturally adherent cells which need attachment to a surface for their growth, are grown in the appropriate cell cultivating system containing commercially available micro spherical beads to which the cells adhere during the growth.

In yet another preferred embodiment of the invention, the naturally adherent cells which need attachment to a surface for their growth, are grown in the cell culture flasks with a subsequent detachment of the cells from the flask bottom with an appropriate detaching reagent.

In accordance with the present invention, either eukariotic or prokariotic cells can be used. In addition, the variety of compounds having biologically relevant activity may be used including but not limited to neurotransmitters, hormones, toxins, receptor activators and inhibitors, ion channels and ion pump modulators, irritants and/or drugs.

The cells grown in accordance with the preferred embodiments described above, are mixed with an appropriate fluorescent dye, for example FURA-2AM for measurements of concentrations of intracellular calcium or BCECF-AM for measurements of intracellular pH, and are incubated in the appropriate conditions to allow the dye to penetrate into the cell. The cells loaded with a dye are supplied to the apparatus. In the apparatus, the cells are successively mixed with a solutions of the compounds to be tested.

One aspect of the present invention is a method for identifying compounds having biological activity, comprising the steps of: (a) combining a homogeneous suspension of living cells with a test compound having an unknown cellular effect to form a test mixture, (b) directing the test mixture through a detection zone; and (c) measuring a cellular response of the suspended cells to the test compound as the test mixture is flowing through the detection zone. The method will often include the additional steps of: (d) combining a homogeneous suspension of the cells with a standard compound having a known effect on the cellular response of the cells to form a standard mixture; (e) directing the standard mixture through the detection zone; and (f) measuring the cellular response of the cells to the standard compound. In one embodiment, the standard compound and the test compound are simultaneously mixed with the cells in the combining steps, and the measuring step detects the known effect or an alteration of the known effect. The standard compound can be an agonist or antagonist of the cellular response. In one mode of operation, steps (a) and (d) are performed simultaneously; steps (b) and (e) are performed simultaneously; and steps (c) and (f) are performed simultaneously using a single suspension of the cells. In another mode of operation, steps (a), (b), and (c) are performed first, and then steps (d), (e), and (f) are performed, wherein the test compound is added together with the standard compound in step (d). If the cellular response is detected in step (c) to indicate that the test compound is active to generate the response, and the standard compound is an antagonist, then a decrease in the cell response from step (c) to step (f) is indicative that the test compound is an agonist of the known effect. If the cellular response is not detected in step (c), indicating that the test compound is not active to generate the response, and the standard compound is an agonist, then an alteration of the known effect detected in step (f) is indicative that the test compound is an antagonist of the know effect. Preferably, the method is performed automatically under the direction of a programmable computer on a plurality of test compounds and a plurality of standard compounds, and a successive series of antagonists are automatically added as the standard compound in step (d) if the cellular response is detected in step (c) to indicate that the test compound is active to generate the cellular response, whereby a decrease in the cellular response detected in step (f) is indicative that the test compound is an agonist of the known effect; and a series of agonists are automatically added as the standard compound in step (d) when the cellular response is not detected in step (c), whereby an alteration of the known effect detected in step (f) is indicative that the test compound is an antagonist of the known effect.

In one embodiment of the method, if step (f) indicates that the compound is an agonist of the known effect, then the method includes automatically determining the concentration dependence of agonist activity of the test compound by repeating steps (a), (b), and (c), and (d), (e), and (f) while varying the concentration of the test compound and the standard compound and recording resultant changes in the cellular response; and if step (f) indicates that the compound is an antagonist, then the method includes automatically determining the concentration dependence of inhibition of the cellular response in the presence of the agonistic standard compound by repeating steps (d), (e), and (f) while varying the concentration of the test compound and the standard compound and recording resultant changes in the cellular response. Optionally, the method also comprises the step, when step (f) indicates that the compound is an antagonist, of: (g) automatically determining the concentration dependence of cell response activation by repeating steps (d), (e), and (f) for a zero concentration of the test compound while varying the concentration of the standard compound and recording resultant changes in cellular response, and then repeating this step (g) for different concentrations of the test compound. The method may further include the step when step (f) indicates that the compound is an agonist, of: (h) automatically determining the concentration dependence of cell response activation by repeating steps (d), (e), and (f) for a zero concentration of the standard compound while varying the concentration of the test compound and recording resultant changes in cellular response, and then repeating this step (h) for different concentrations of the compound. Variation of the concentration of the test compound and/or the standard compound can be done continuously or in a stepwise manner. One preferred step includes graphically displaying the recorded changes in the cellular response.

The cellular response can be any desired cellular response susceptible of being measured or detected as the cells flow past a detector in suspension. It can be evidenced by analyzing the cells themselves or the medium in which the cells are suspended. Cellular responses can be measured, for example, from a change in intracellular ion concentration, such as calcium, magnesium, proton, sodium, or potassium. In one embodiment, the ion is detected using an intracellular dye such as a visible and/or fluorescent dye.

The invention also includes an apparatus for automatically measuring the effect of a plurality of test compounds on living cells, comprising: a test compound sampler for sequentially providing samples of multiple test compounds, a cell suspension input for providing a homogeneous suspension of living cells, a mixing chamber, coupled to the test compound sampler, for receiving the samples of the test compounds from the test compound sampler, and receiving the suspension of living cells from the cell suspension input and mixing each test compound with the suspension of living cells; and a detector, coupled to the mixing chamber, for measuring a cellular response of the suspended cells to each test compound. The apparatus may additionally include a standard compound sampler, coupled to the mixing chamber, for providing a sample of a standard compound having a known effect on the cellular response of the suspended cells, wherein the mixing chamber receives the sample of the standard compound from the standard compound sampler and mixes the standard compound with the suspended cells and the detector measures the cellular response of the suspended cells to the standard compound. In one embodiment, the mixing chamber simultaneously mixes the test compound and the standard compound with the suspended cells and the detector detects the known effect or an alteration of the known effect. The apparatus may also include a first gradient device, coupled to the test compound sampler, for automatically adjusting the concentration level of the test compound transferred to the mixing chamber from the test compound sampler; and a second gradient device, coupled to the standard compound sampler, for automatically adjusting the concentration level of the standard compound transferred to the mixing chamber from the standard compound sampler. The apparatus may further include a switching valve, coupled to the first and second gradient devices at an input of the switching valve and coupled to the mixing chamber at an output of the switching valve, for selectively switching the flow of a concentration of the test compound or a concentration of the standard compound or both to the mixing chamber where the test compound and/or the standard compound is then mixed with the suspension of cells. In addition, the apparatus may include a calibration unit, coupled to the switching valve, wherein the switching valve also selectively switches the flow of a calibration solution provided by the calibration unit into the mixing chamber where the calibration solution is mixed with the suspension of cells.

The reaction time of the cells with the various test and standard compounds may be controlled through use of various lengths of reaction developing lines coupled to the output of the mixing chamber, for receiving a mixture of the cell suspension mixed with either the test compound, the standard compound or the calibration solution, and providing a flow path for the mixture such that there is adequate time for the suspension cells to react with the test compound, the standard compound or the calibration solution, wherein the reaction developing lines is further coupled to the input of the detector which receives the mixture from the reaction developing lines. In one preferred embodiment, the detector detects changes in intracellular ion concentration. Preferred ions are described above.

The apparatus may additionally include a controller, coupled to the first and second gradient devices, the test compound sampler, the standard compound sampler and the switching valve, for controlling their operation; and a computer, coupled to the controller, for sending command signals to the controller in accordance with a software program implemented by the computer, wherein the computer is also coupled to the detector in order to send and receive cell response measurement signals to and from the detector. In order to automate the apparatus further, the test compound sampler can be an automated robotic sampler capable of selecting a specified test compound from a library of test compounds. A controller can be coupled to the test compound sampler, for controlling the operation of the test compound sampler, using the computer, coupled to the controller, for sending command signals to the controller in accordance with a software program implemented by the computer, thereby controlling the selection and retrieval of test compounds by the test compound sampler from the test compound library.

The apparatus can direct flow through the various elements under either positive or negative pressure. Thus, one embodiment includes a gradient pump having an input and an output, coupled to the test compound sampler, for adjusting the concentration level of the test compound transferred to the mixing chamber from the test compound sampler, wherein the test compound sampler comprises a first intake nozzle for receiving the specified test compound, a second intake nozzle for receiving a buffer solution; and wherein the gradient pump is coupled to the first and second intake nozzles and receives specified concentrations of the test compound by adjusting the amount of test compound and buffer solution received by the first and second intake nozzles, respectively, wherein the buffer solution is a diluting agent of the test compound. This embodiment may also include a standard compound sampler for providing a sample of a standard compound to the mixing chamber. The standard compound sampler is preferably an automated robotic sampler capable of selecting a specified standard compound from a library of standard compounds. The apparatus may also include a second gradient pump having an input and an output, coupled to the standard compound sampler, for adjusting the concentration level of the standard compound provided to the mixing chamber from the standard compound sampler, wherein the standard compound sampler comprises a third intake nozzle for receiving the specified standard compound, a fourth intake nozzle for receiving a buffer solution; and wherein the second gradient pump is coupled to the third and fourth intake nozzles and receives specified concentrations of the standard compound by adjusting the amount of standard compound and buffer solution received by the third and fourth intake nozzles, respectively, wherein the buffer solution is a diluting agent of the standard compound. The apparatus may further comprise a second mixing chamber coupled to the outputs of the first and second gradient pumps, for receiving and mixing the specified concentrations of the specified test compound and the specified standard compound, such that the output of the second mixing chamber is provided to the first mixing chamber. Another element that can be included is a calibration unit for providing a calibration solution; and a switching valve, having a first input coupled to the second mixing chamber, a second input coupled to the calibration unit, and an output coupled to the first mixing chamber, for switching between the flow of either a compound mixture from the second mixing chamber or the calibration solution from the calibration unit and then providing the flow to the first mixing chamber where it may be mixed with the cell suspension. Preferably, the calibration unit comprises a calibration maximum solution which provides for maximal cell response when mixed with the cell suspension, a calibration minimum solution which provides for minimal cell response when mixed with the cell suspension, a diverting valve having a first input coupled to the calibration maximum solution and a second input coupled to the calibration minimum solution, for switching between the flow of either the calibration maximum solution or calibration minimum solution; and a pump, coupled to the output of the diverting valve and an input of the switching valve, for pumping either the calibration maximum or calibration minimum solution from the diverting valve into the switching valve. The positive pressure version of the apparatus can also include a second pump, coupled to an input of the first mixing chamber, for pumping the suspension of cells from the cell suspension input into the first mixing chamber. Reaction developing lines, having an input coupled to an output of the first mixing chamber and an output coupled to an input of the detector, for providing a flow path and a reaction time delay for a mixture received from the first mixing chamber and for providing the mixture to the detector, can also be included.

In a preferred embodiment, as above, the apparatus can include a controller, coupled to the first and second gradient pumps, the test compound sampler, the standard compound sampler and the switching valve, the first and second mixing chambers, the first and second pumps and the diverting valve for controlling their operation; and a computer, coupled to the controller, for sending command signals to the controller in accordance with a software program implemented by the computer, wherein the computer is also coupled to the detector in order to send and receive cell response measurement signals to and from the detector.

The apparatus of the present invention can also be run under negative pressure by utilizing a pump, coupled to the output of the detector, for providing negative pressure to the apparatus, a proportionating valve, coupled to the test compound sampler, for adjusting the concentration level of the test compound transferred to the mixing chamber from the test compound sampler, wherein the test compound sampler further comprises a first intake nozzle for receiving the specified test compound, a second intake nozzle for receiving a buffer solution; and the proportionating valve receives specified concentrations of the test compound by adjusting the amount of test compound and buffer solution received by the first and second intake nozzles, respectively, wherein the buffer solution is a diluting agent of the test compound. The negative pressure apparatus can also include an automated standard compound sampler capable of selecting a specified standard compound from a library of standard compounds, the standard compound sampler including a third intake nozzle for receiving the specified standard compound and a fourth intake nozzle for receiving a buffer solution; and a second proportionating valve, coupled to the third and fourth intake nozzles, for receiving specified concentrations of the standard compound by adjusting the amount of standard compound and buffer solution received by the third and fourth intake nozzles, respectively, wherein the buffer solution is a diluting agent of the standard compound. In one version, the apparatus includes a first priming valve, coupled to the output of the first proportionating valve, for receiving the specified concentration of the test compound and providing the test compound to the mixing chamber, and a second priming valve, coupled to the output of the second proportionating valve, for receiving the specified concentration of the standard compound and providing the standard compound to the mixing chamber. A calibration unit can be included as described previously, as can reaction developing lines, robotic input, and computer control. The cell suspension input may comprise a cell suspension reservoir, a buffer reservoir, a third diverting valve, having a first input coupled to the cell suspension reservoir and a second input coupled to the buffer reservoir, for adjusting the concentration of the cell suspension, wherein the buffer is a diluting agent of the cell suspension, and a fourth priming valve, coupled to the output of the third diverting valve, for receiving the cell suspension mixture from the third diverting valve and providing this mixture to the second mixing chamber.

Certain preferred embodiments of the present invention are discussed below in more detail in connection with the drawings and the detailed description of the preferred embodiments. These preferred embodiments do not limit the scope or nature of the present invention.

BRIEF DESCRIPTION OF THE DRAWINGS

FIG. 6 comprises the combination of FIGS. 6a–6d FIG. 7 comprises the combination of FIGS. 7a–g.

FIG. 8 comprises the combination of FIGS. 8a–e.

FIG. 9 represents the experimental results of ET-1 dose dependent $Ca^{2+}$ mobilization in the presence of BQ-123.

FIG. 10 represents the experimental results of dose dependent inhibition of ET-1 induced $Ca^{2+}$ mobilization in the TE-671 cells with BQ-123.

DESCRIPTION OF THE PREFERRED EMBODIMENTS

Figure 1:
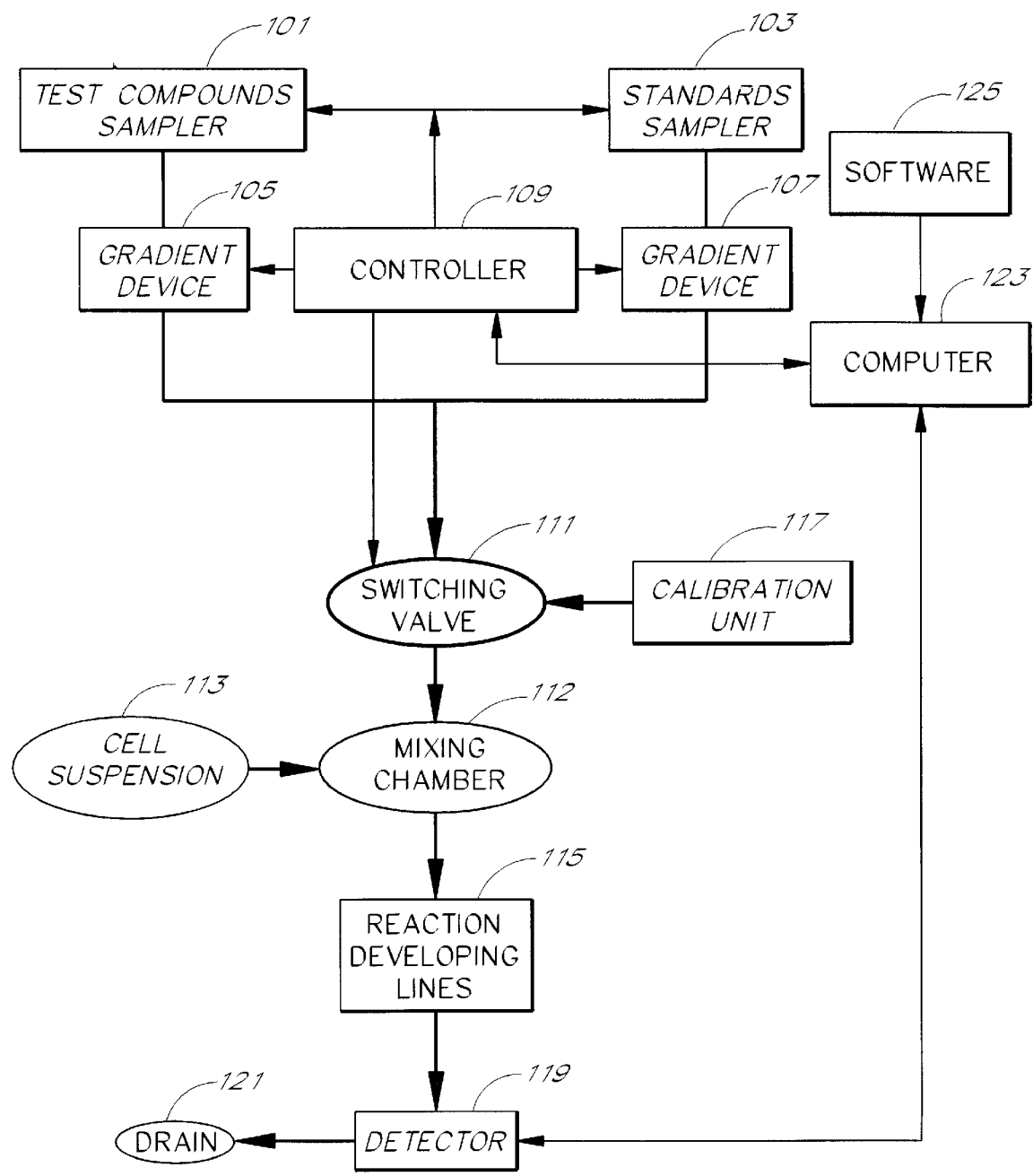
FIG. 1 is a block-diagram of one embodiment of the combinatorial screening apparatus of the present invention.

The present invention provides for real-time, continuous monitoring and detection of the physiological or pharmacological effect of a test compound on living cells. In its simplest embodiment, the present invention comprises a method and apparatus for continuously contacting a flow of suspended living cells with a predetermined concentration of at least one potentially active compound, preferably with predetermined concentrations of at least two active compounds. Then, intracellular changes that occur in response to contact between the cells and the active compounds are continuously measured as the flow of living cells and compounds passes a detector.

It is contemplated that the present invention will be of major value in highthroughput screening; e.g., in screening a large number of candidate compounds for activity. It has particular value, for example, in screening synthetic or natural product libraries for active compounds.

In one preferred embodiment, a test compound, a standard compound, and a cell suspension are continuously mixed together and, after an incubation period, are passed by a detector that measures the concentration in the cells or in the intracellular medium of at least one analyte. In one embodiment, the concentration of the test compound and/or the standard compound is varied over time to generate dose/response curves as output from the detector.

It is preferred that the apparatus of the present invention is under the control of a computer or other programmable controller. The controller can continuously monitor the results of each step of the process, and can automatically alter the testing paradigm in response to those results.

The incubation period after mixing of the compound or compounds and the cells can advantageously be controlled by passing that mixture through a length of tubing connecting the mixing chamber with the detector. The incubation period will thus be determined by the flow rate and the length of the tubing. Incubation periods can vary by several orders of magnitude, depending on the particular analyte and the resultant reaction time. For example, the incubation period could be as little as one second or a fraction of a second for rapid or short-lived physiological responses, or as long as several minutes or even hours.

The analyte can be any analyte that is readily detectable by detectors and/or detector/chemistry combinations. Thus, various ion or electrolyte concentrations, colorimetric changes, optical density changes, fluorescence, luminescence, pH, gas production, and the like are all readily adaptable for use in the present method and apparatus.

In detecting ion or electrolyte changes, calorimetric or fluorescent dyes are one particularly preferred embodiment. For example, calcium ion is detectable by such probes as Fura-2, Indo-1, Fura Red or Quin-2, sodium ions by SBFL, proton ions by BCECF, SNAFL, DM-NERF, magnesium ions by Mag-Fura-2 or Mag-Fura-5, chloride ions by SPO, SPA or MOAE. All these dyes are commercially available, for example, from Molecular Probes, Inc., Oreg.

FIG. 1 illustrates a schematic configuration of a preferred embodiment of an apparatus of the present invention. The preferred embodiment consists of a test compound sampler 101, for receiving and holding a sample of a compound to be tested; a standards sampler 103, for receiving and holding a sample of a standard solution (e.g., a buffer and/or a known agonist or antagonist) to be mixed with the compound to be tested; a concentration gradient device 105 connected to compound sampler 101 for controlling the flow volume of the compound to be tested; a concentration gradient device 107, connected to standards sampler 103, for controlling the flow volume of the standard solution; a switching valve 111 for receiving a compound/standard solution mixture or a calibration solution and for directing them to the mixing chamber 112 for mixing one of these solutions with a cell suspension; a cell suspension 113; a calibration unit 117, for supplying calibration solutions to the switching valve 111 so that the calibration solutions may be mixed with the cell suspension in predetermined ratios; a reaction developing lines unit 115, for receiving the cell suspension mixed with either the compound/standard solution mixture or the calibration solution and for transferring this mixture to a detector 119; and a drain 121 for receiving and draining the mixture from detector 119 after the cell response has been detected and measured by detector 119. A controller 109 is coupled to the test compound sampler 101, the standards sampler 103, gradient devices 105 and 107 and switching valve 111. The controller controls the above devices by receiving command signals from a computer 123 which in turn generates, sends and receives signals in accordance with a software program 125.

After a compound and/or standard is mixed with cells in mixing chamber 112, which is readily commercially available and in the preferred embodiment is the static mixer 125-1345 (Bio Rad), this mixture is then sent through reaction developing lines 115 so that it may be mixed more thoroughly and provided with enough time for its reagents to thoroughly react with one another. The detector 119, is connected to the reaction developing lines unit 115, and receives the cell/compound/standard mixture from the reaction developing lines 115.

In a preferred embodiment, each of the samplers 101 and 103 include a sipper nozzle which may be positioned into a vial containing a respective compound or standard solution. These samplers are well-known in the art and are readily available commercial products, e.g. A/S 300 Autosampler, Catalog # 15006330, Scientific Measurement Systems, Inc., Colo. For handling multiple samples, conventional automated or robotic equipment (not shown) may be used to supply the apparatus with the samples. Banks of different samples, arranged in 48 or 96 well plate format for example, can easily be accommodated by such automated sampling equipment.

The gradient devices 105 and 107 are also readily available commercial devices, e.g., GP40 Gradient Pump (Dionex). Depending on the mode of action, the corresponding concentration gradient devices 105 and 107 can prepare either discrete concentrations or continuous gradients of concentrations of the compound to be tested or the standard substance (agonist or antagonist) by diluting them with buffer. For example, if a continuous curve of cell response versus compound concentration in the presence of a standard substance is desired, the computer 123 will instruct the controller 109 to control the gradient devices 105 and 107 in such a way that continuous gradients of respective compound and a predetermined constant concentration of standard solution are provided to switching valve 111. Alternatively, if a continuous curve of cell response versus standard solution concentration in the presence of a compound is desired, the computer 123 will instruct the controller 109 to control the gradient devices 105 and 107 such a way that continuous gradients of the respective standard solution and a predetermined constant concentration of the respective compound are provided to switching valve 111.

The calibration unit 117, connected to the switching valve 111, supplies calibration solutions needed to calibrate the output signal, MAX and MIN, of the apparatus. In a preferred embodiment, this calibration unit consists of a diverting valve which is a readily available commercial device, e.g,. the SV3-2 Diverter Valve, (BioRad). The diverter valve alternates supply of two calibration solutions to the switching valve 111. The switching valve 111 combines outflows from the gradient devices 105 and 107 or, alternatively, from the calibration unit 117 with a cell flow from a cell suspension reservoir 113 and directs the mixed flow into one of the reaction developing lines 115. The switching valve 111 is of a type which is well-known in the industry and in a preferred embodiment is the 3-way microvalve 4-8-900 manufactured by General Valve Corp. The cell suspension reservoir 113 is also of a type which is well known in the art and in a preferred embodiment is a regular glass beaker. Cells are maintained in suspension pending introduction into the device by simple low shear stirring.

The reaction developing lines 115 are typically tubes made from a non-corrosive material, having a specified diameter, through which the above mentioned mixture of cell suspension, compound and standard solution may flow. For example, polyethylene, polypropylene, or polytetrafluoroethylene tubing can be used. Tubing to which cells and other reagents will not stick is particularly preferred. The diameter of the tubing is a matter of choice. Capillary tubing having an inner diameter of from about 0.2 mm to about 2 mm is particularly advantageous, because it allows the use of very small sample sizes.

This tubing is typically set in a winding configuration so that as the mixture flows through it, the mixture is thoroughly agitated and mixed. Even if the mixture is well mixed before introduction into the tubing, a spiral or wound configuration allows long tubing lengths in a compact area. These reaction developing lines 115 are commercially available and in one embodiment may be formed by Teflon tubing.

The mixture of cell suspension and compound/standard solution, also referred to as "reaction suspension," enters the detector's flow-through optical cell or other detection zone with a time delay or incubation period determined by the length of the reaction developing line 115. Once the reaction suspension reaches detector 119, the detector 119 can measure the cell suspension response to the specified concentration of the test compound. In a preferred embodiment, the detector 119 measures a fluorescence signal from the calcium sensitive dye, FURA 2, spectral characteristics of which depend on a concentration of the intracellular ionized calcium, in order to determine the level of cell activity. In order to make this measurement, the detector 119 alternately irradiates the reaction suspension passing through a flow-through optical quvette, with the light of the wavelengths 340 nm and 380 nm and measures fluorescence intensity at 540 nm. The ratio (R) of the fluorescence intensities registered at 540 nm upon excitation at 340 nm and 380 nm, respectively, is transmitted to the computer 123. The computer 123 calculates the concentration of the intracellular ionized calcium in accordance with the following equation which is well-known in the art:

$$[Ca^{2+}] = K_d (R-R_{min})/(R_{max}-R)(I_f/I_b)$$

where $K_d$ is the dissociation constant of calcium/FURA 2 complex and $R_{min}$ and $R_{max}$ are the ratios obtained in the presence of the calibration solutions MIN and MAX, respectively, and $I_f$ and $I_b$ are the fluorescence intensities measured at 540 nm upon excitation at 380 nm in the presence of calibration solutions MIN and MAX respectively. A computer 123, connected to the detector 119, dictates its operation. The computer 123 is also connected to or is a part of the controller 109 which controls the first and second gradient devices 105 and 107, switching valve 111 as well as test compound sampler 101 and standard sampler 103 in accordance with a software 125 implemented within the computer 123. The detector 119 is capable of measuring the particular desired signal, whatever its origin. An optical detector 119, may be a spectrophotometer, spectrofluorometer, or a luminometer, each of which have a flow-through optical cell. these devices are well-known in the art and are commercially available. For example, one embodiment of the apparatus of the present invention may use an AMINCO-Bowman Series 2 Luminescence Spectrofluorometer (Fa-256, Spectronic Instruments, Inc.). If the detector is a direct ion measuring device, it can, for example, comprise a pH sensor or an ion selective electrode. Sodium, calcium, and potassium detectors are examples of such devices. Detectors of this type are commercially available. All of these devices can be controlled by means of a computer 123 during the data acquisition process.

The apparatus of the present invention is contemplated in two different specific embodiments. A positive pressure system may be created with piston pumps or other suitable pumps supplying reagents under positive pressure. Alternatively, a negative pressure system may be created with a peristaltic pump or other suitable pump drawing reagents through the system. The negative pressure system is the simplest embodiment, because a large number of input sources can be driven by a single downstream pump.

Figure 2:
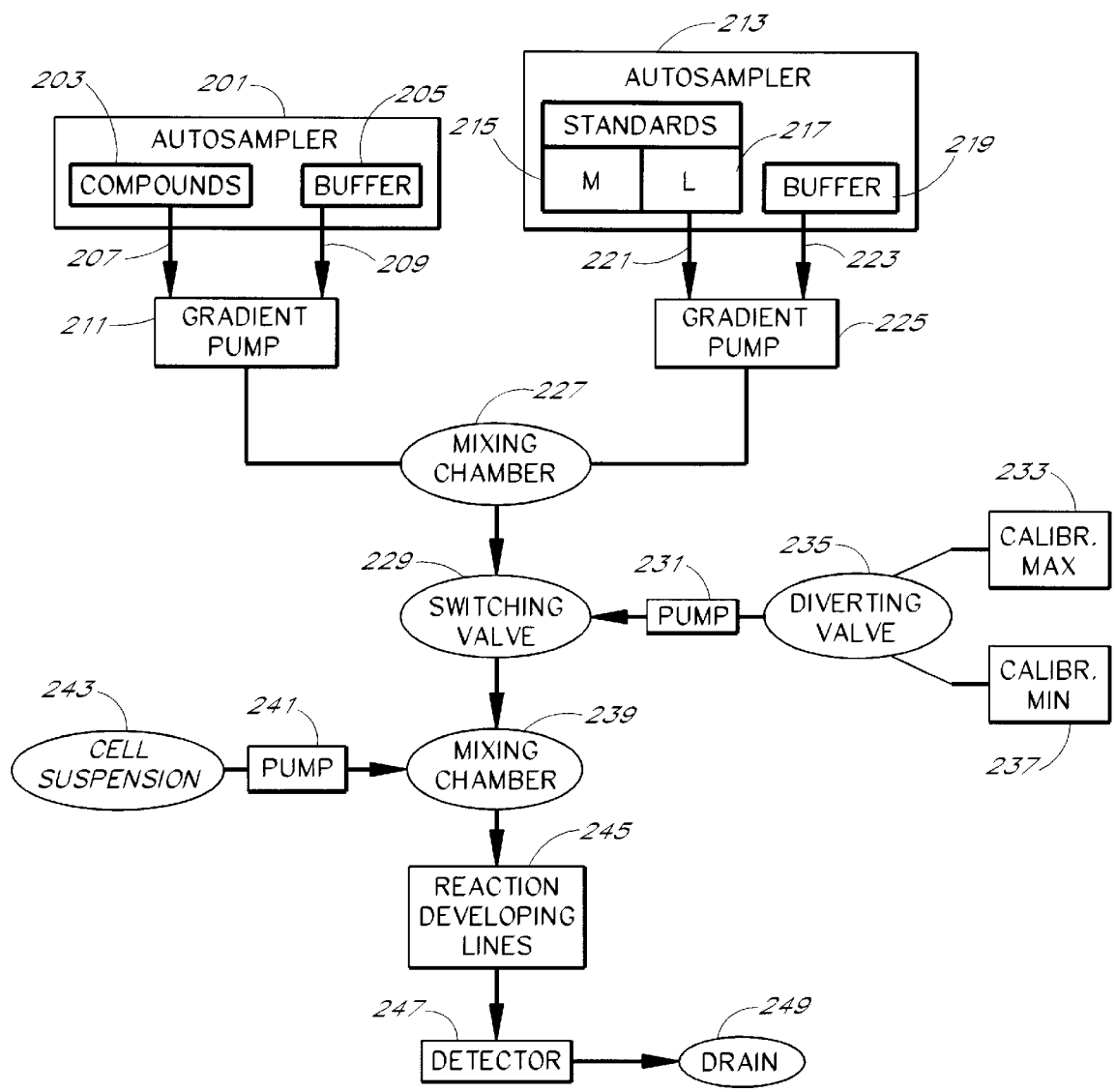
FIG. 2 is a block-diagram of a positive pressure fluidic system which may be used in a combinatorial screening apparatus of the present invention.

FIG. 2 illustrates a schematic configuration of one embodiment of a positive pressure fluidic system. In a preferred embodiment, this system operates automatically under the control of a programmable controller, as will be explained in more detail below. This embodiment includes an autosampler 201 which holds one or more compounds to be tested 203 and buffer 205 which may be mixed with the compound 203 in order to provide various concentrations of the compound 203; intake nozzles, or ports, 207 and 209 for receiving a compound and buffer, respectively and delivering the same to a gradient pump 211 which controls the concentration level and flow of a test compound 203 into a mixing chamber 227; an autosampler 213 which holds one or more standards (i.e., antagonists 215 and/or agonists 217) and a buffer 219 which may be mixed with the standard 215 or 217, in order to provide various concentrations of the standard; intake nozzles, or ports, 221 and 223, for receiving a standard and buffer, respectively, and providing the same to a gradient pump 225 which controls the concentration level and flow of a standard solution (agonist or antagonist) into the mixing chamber 227. Each of the gradient pumps, 211 and 225, respectively, may advantageously have two inlet tubing lines and one outlet tubing line, the outlet tubes being connected to each other through the mixing chamber 227. A controller (109 of FIG. 1) which is not shown in FIG. 2 controls the operation of autosamplers 201 and 213 and gradient pumps 211 and 225 by supplying remote signals to start/stop the pumping. In a preferred embodiment, gradient pumps 211 and 225 may be the GP 40 Gradient Pump manufactured by Dionex.

The mixing chamber 227 receives the compound solution flowing through gradient pump 211 and, optionally, a standard solution flowing through the gradient pump 225, and mixes the compound and standard substances together. A diverting valve 235 alternates the supply of either the calibration solution for maximal response 233 or the calibration solution for minimal response 237. The diverting valve 235 preferably includes two inlet tubes, one tube for each of the two different calibration solutions 233, 237, and one outlet tube connected to a pump 231. The diverting valve 235 is well-known in the art and can be implemented by the SV-3 Diverter Valve (BioRad). The controller (109 of FIG. 1) which is not shown in FIG. 2, sends signals to the diverter valve 235 which switches intake ports to connect one calibration solution 233 or another, 237, to the intake of the pump 231. The pump 231 for supplying calibration solutions to the fluidic system is also shown in FIG. 2. The pump 231 receives either the calibration max. solution 233 or the calibration min. solution 237 from diverting valve 235 and then pumps the received calibration solution to switching valve 229. The outlet tube of pump 231 is connected to an input of the switching valve 229. The pump 231 is advantageously a standard piston pump which is well-known in the art. In a preferred embodiment, the pump 231 is the series 1350 Soft-Start Pump (BioRad). The switching valve 229 alternates the supply of either the compound/standard mixture or one of the calibration solutions to a mixing chamber 239. A pump 241 supplies cells from cell suspension 243 to the mixing chamber 239. The pump 241 receives cells from cell suspension 243 from an inlet tube and pumps the received cells through an outlet tube to one intake of the mixing chamber 239. The compound/standard solutions or calibration solutions come through another intake of mixing chamber 239. Both mixing chambers 227 and 239, are well known in the art and in a preferred embodiment may be implemented by the Static Mixer, 125-1345 (BioRad). The pump 241 can be a standard piston pump which is well-known in the art. In a preferred embodiment, the pump 241 is the series 1350 Soft-Start Pump (BioRad). The mixture of cells and compound/standard solution or cells and a calibration solution is then fed from mixing chamber 239 to reaction developing lines 245. The length of these lines, combined with the flow rate, determines the incubation period; i.e., the time elapsed from the point where the cells are mixed with the compound/standard mixture or the calibration mixture to the point of reaching detector 247. The detector 247 then measures the amount of cell response due to the compound/standard mixture or the calibration solution. After the cell response has been measured by detector 247, the mixture is then drained from the detector via drain 249.

Figure 3:
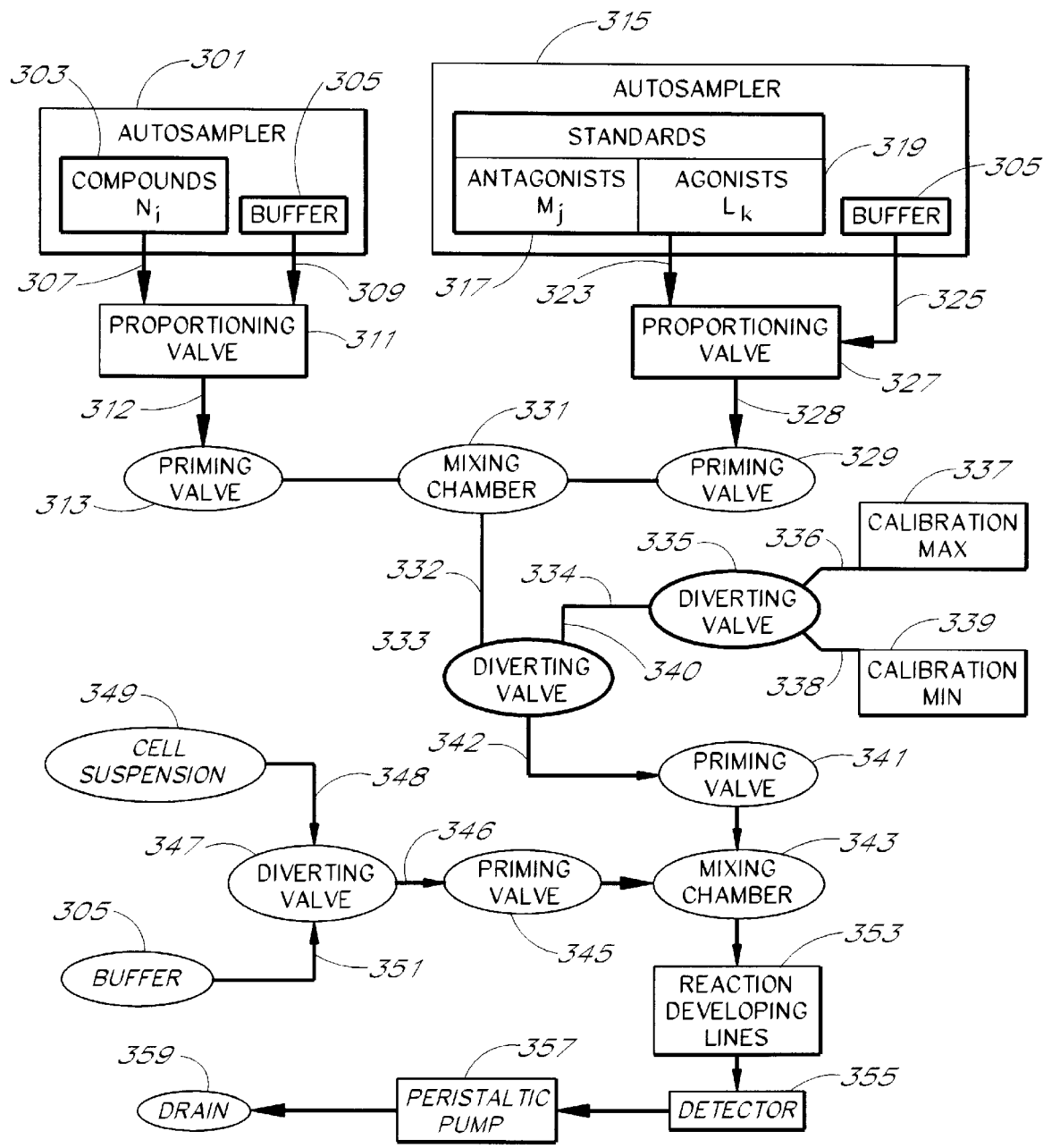
FIG. 3 is a block-diagram of one embodiment of a preferred system which may be used in a combinatorial screening apparatus of the present invention.

FIG. 3 illustrates a schematic configuration of a preferred embodiment of the negative pressure fluidic system. As shown in FIG. 3, one preferred embodiment includes an autosampler 301 which holds one or more compounds ($N_i$) 303 and a buffer 305, the autosampler 301 further including two intake nozzles, or ports, 307 and 309, for receiving the compound ($N_i$) 303 and buffer 305, respectively; a proportionating valve 311 for preparing dilutions of the compound 303 with the buffer 305 in predetermined or specified proportions and delivering this mixture to a priming valve 313; an autosampler 315 which holds standard antagonists ($M_j$) 317 agonists ($L_k$) 319 and the buffer 305, the autosampler 315 further including two intake nozzles 323 and 325 for receiving the standard and the buffer, respectively; a proportionating valve 327 for preparing dilutions of the standard substance 317 or 319 with buffer 305 in predetermined or specified proportions and delivering this mixture to a priming valve 329. The proportionating valves 311 and 327 may be of any type which is well-known in the art. In a preferred embodiment these valves 311 and 327 are the series 4 miniature solenoid type valves (4-8-900 General Valve Corp.) working in a proportioning frequency mode. Similarly, priming valves 313 and 329 may be of any "normally opened" type which is well-known in the art and, in a preferred embodiment, are the series 4 miniature solenoid type valves (4-39-900) manufactured by General Valve Corp.

A mixing chamber 331 mixes a compound solution received from priming valve 313 and a standard solution received from priming valve 329. The first mixing chamber 331, as with the other mixing chambers discussed herein, can constitute a simple "Y" connector; a chamber having a diameter several times that of the tubing; a length of tubing; a serpentine, baffled chamber; a chamber containing a mechanical rotating mixer; or any other suitable structure. Typically, the method will involve very small quantities of liquid (e.g., a full concentration gradient run can be accomplished with as little as 0.3 ml of sample). Thus, the volumes to be mixed are small and the mixing chamber should have small internal volume and high mixing efficacy. These types of mixers are well known in the art and in a preferred embodiment may be implemented by the Visco Jet® Micro-Mixer (#TCMA0120113T) manufactured by The Lee Company.

A diverting valve 335 alternates the supply of either a calibration solution for maximal response 337 or a calibration solution for minimal response 339. The diverting valve 335 includes two inlet tubes for receiving the two different calibration solutions and one outlet tube connected to another diverting valve 333. The diverting valve 333 can have two inlet tubes, one for receiving a compound/standard solution mixture and the other for receiving one of the calibration solutions 337 or 339. The diverting valve 333 then alternates the supply of either the compound/standard mixture or one of the calibration solutions through an outlet tube to a priming valve 341 which then delivers the received fluid to a mixing chamber 343. A third diverting valve 347 alternates the supply of either cells from a cell suspension 349 or the buffer solution 305 through an outlet tubing 346 to a priming valve 345 which then delivers either the cells or buffer to the mixing chamber 343 where it is mixed with either a compound/standard mixture or one of the calibration solutions received from priming valve 341. The diverting valves 333, 335 and 347 may be of any type which is well known in the art, for example, a SV-3 Diverter Valve (BioRad). This mixture is then sent to reaction developing lines 353 which determine the time elapsed from the point where the cells are mixed with the compound/standard mixture or one of the calibration solutions to the point where the mixture reaches the detector optical cell 355. As explained above, the reaction developing lines 353 and the detector 355 may be of any type which are well-known in the art.

A peristaltic pump 357, used as a negative pressure pump, can advantageously supply the necessary pressure required to make the various solutions and mixtures described above flow through the various valves (311, 313, 327, 329, 333, 335, 341, 345 and 347) mixing chambers (331 and 343), the reaction developing lines 353, the detector 355, and finally to the drain 359. Suitable peristaltic pumps 357 are well-known in the industry and in a preferred embodiment may be implemented by a EP-1 Econo Pump (BioRad). The pumps, valves, detectors, and other active components of the system are preferably under the automated control of a programmable controller, as explained in more detail below.

The apparatus in the present invention preferably has two primary modes of action, a screening mode and a potency mode.

Figure 4:
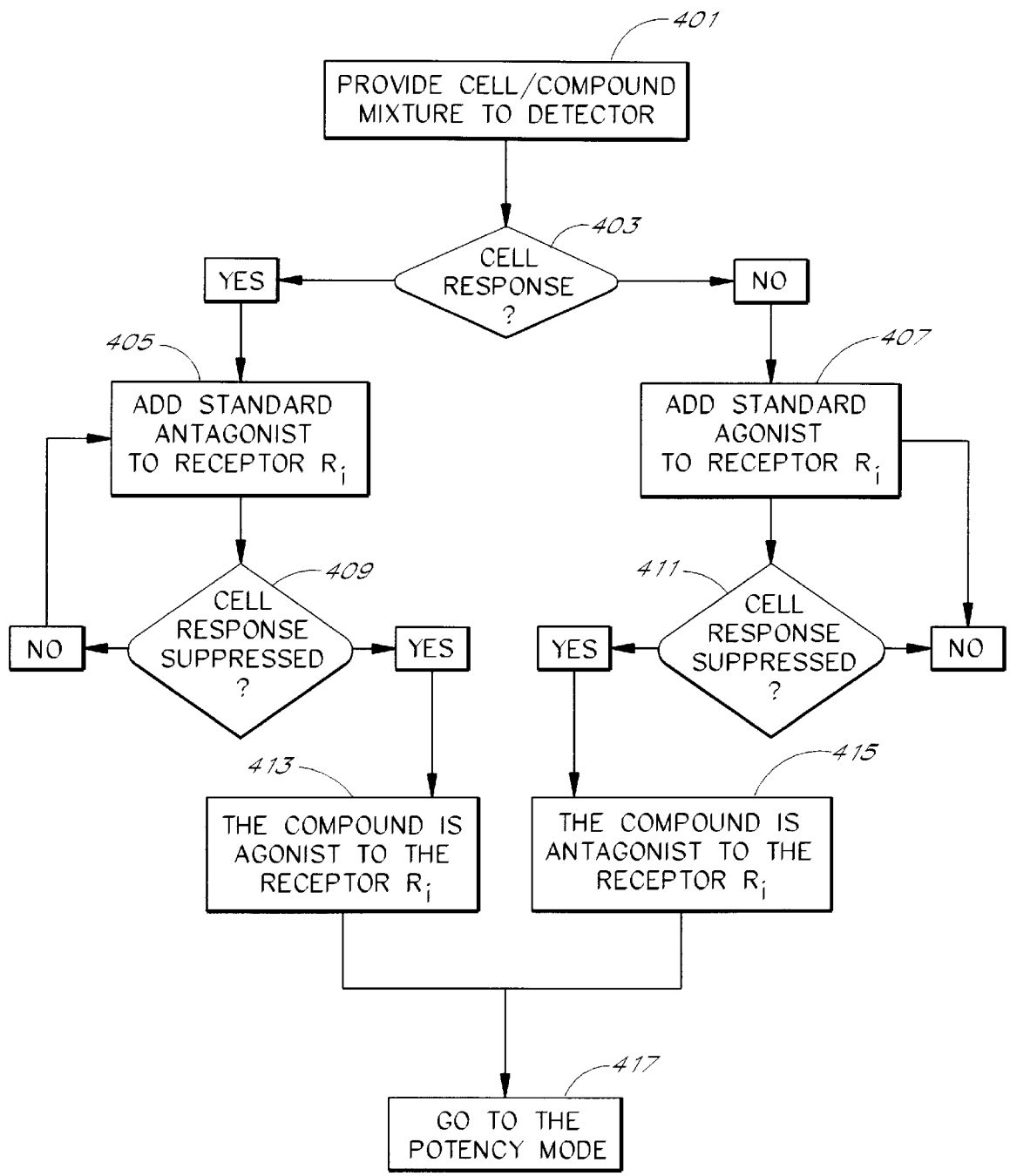
FIG. 4 represents a simplified algorithm of a screening mode which may be utilized in a combinatorial screening apparatus of the present invention.

FIG. 4 shows an algorithm that may be used in the invention to detect cell response during the screening mode. First, a cell/compound mixture is provided to a detector (step 401). Next, the apparatus determines if the compound, upon contact with the cells, triggers any cell response (step 403). There are two possibilities: either the compound does not produce any response (NO), or it induces the cell response (YES). Cell response is determined by monitoring the signal from the detector for the particular analyte being detected. The control system first calibrates to establish a baseline and a maximal response, and any signal from the detector falling between those values is considered to be a positive response.

If the compound causes no cell response, (NO), as measured by the monitoring part of the apparatus, the cells are successively and automatically brought into contact with a mixture of the compound and the standard substances from a predetermined set of agonist solutions (step 407). Each solution in the set contains one or more ingredients that initiates cell response in the absence of the test compound, e.g., through the stimulation of a known cell receptor, ion pump or ion channel molecules. Next, a determination is made as to whether a cell response normally triggered with a particular agonist is suppressed by the particular compound (step 411). The apparatus will keep repeating an admixture of different standard agonist substances with the compound until it detects that the cell response triggered with a particular standard agonist is suppressed in the presence of the compound, or until all agonists available to the machine have been tested. If in step 411, it is determined that a cell response normally triggered with a particular agonist is suppressed by the particular compound (YES), that compound is categorized as an antagonist to the receptor Ri (step 415). After this happens, the instrument is switched over to the potency mode of action if instructed by the software managing the apparatus' performance (step 417).

If the contact of the cells with the compound does initiate the cell response, (YES), as measured by the monitoring part of the apparatus, the cells are automatically brought into contact with successive mixtures of the compound and the standard substance from a predetermined set of antagonist solutions (step 405). Each solution in the antagonist set contains one or more ingredients that block the cell response initiated by at least one known agonist through the stimulation of a known cell receptor, ion pump or ion channel molecules. Next, a determination is made as to whether a cell response triggered with the compound is suppressed in the presence of a particular standard antagonist (step 409). The apparatus will keep repeating an admixture of different standard antagonist substances with the compound until it detects that the cell response triggered with the compound is suppressed in the presence of particular standard antagonist, or until all the antagonists have been tested. If it is determined in step 409, that a cell response triggered with the compound is suppressed by the particular antagonist (YES), that compound will be characterized as an agonist to the receptor Ri (step 413). After this happens, the instrument is switched over to the potency mode of action if instructed by the software managing the apparatus' performance (step 417).

By using known sets of standard agonist and antagonist substances to different receptors, it is possible to screen the compounds against several receptor types and subtypes for specificity and selectivity.

For example, for the endothelin receptor, stimulation of which is indicated by an increase in intracellular concentration of ionized calcium, the following receptor subtype specific antagonists may be used: BQ-123, BQ-788, BQ-153, BQ-485, BMS-182874 PD 151, 242, and the following receptor subtype specific agonists may be used: endothelin-1, endothelin-2, and endothelin-3. Sarafotoxin S6c, IRL 1620, BQ-3020.

For calcium channels, there are sets of channel type specific agonists and antagonists which can be used in a preferred embodiment. For example, agonists of intracellular calcium channels are: Ins $(1,4,5)P_3$, Ryanodine, Caffeine, Heparine, Perchlorate, and their antagonists are: Decavanadte, Ruthenium Red and high concentrations of Ryanodine In another preferred embodiment, the screening mode is used for the characterization of the cell receptor pattern, commonly known as "receptor fingerprinting". In accordance with this embodiment, a particular cell line is screened against standard substances from a predetermined set of agonist solutions. Each solution in the set contains one or more ingredients that initiates cell response through the stimulation of a known cell receptor. When the cells respond to the particular agonist substance, the instrument is switched over to the potency mode of action if instructed by the software managing the apparatus' performance.

Figure 5:
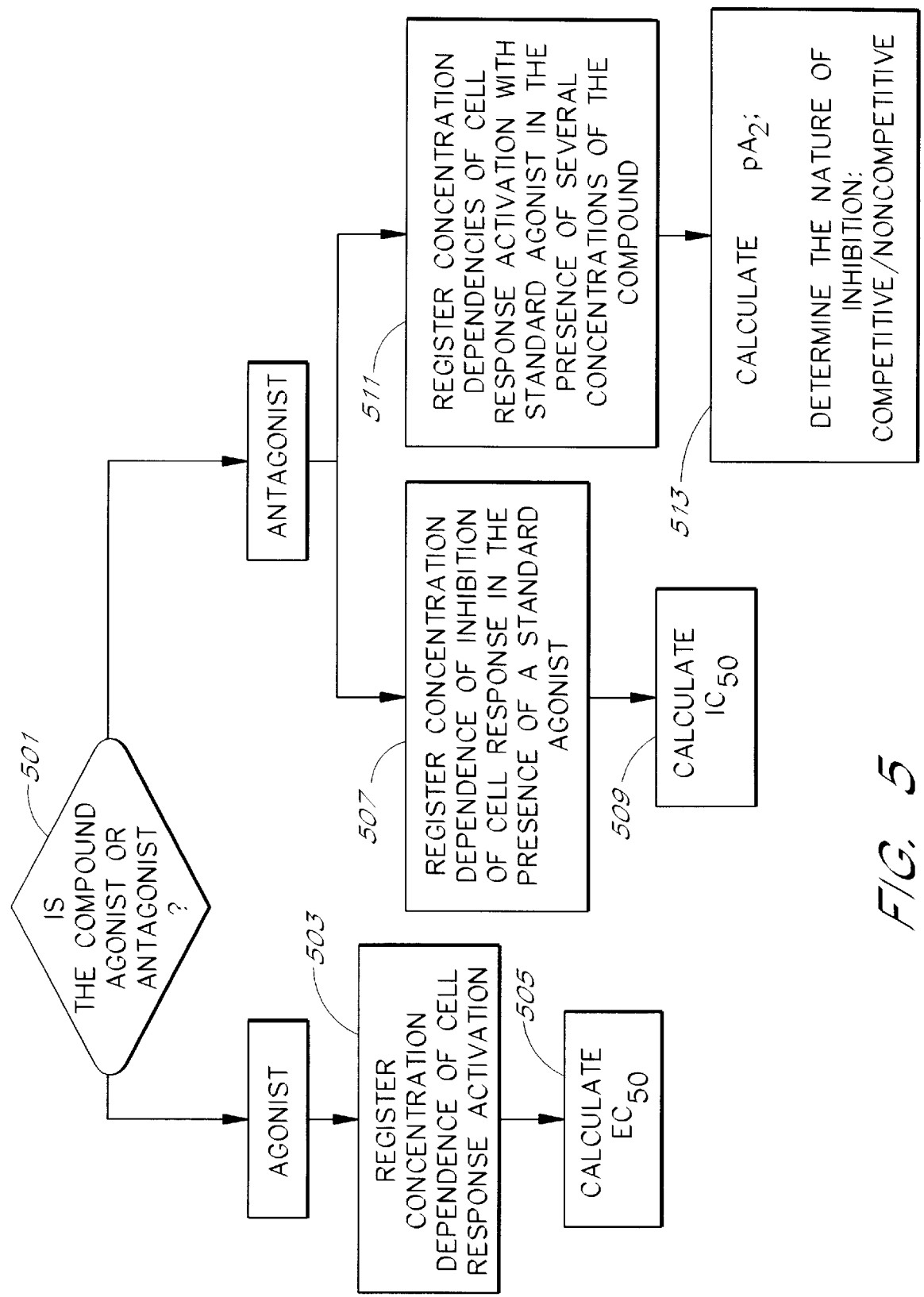
FIG. 5 represents a simplified algorithm for a potency mode which may be utilized in a combinatorial screening apparatus of the present invention.

FIG. 5 shows one algorithm that may be used in the invention in the preferred potency mode. The first step in the potency mode is to determine whether a particular compound has been categorized as an agonist or antagonist (step 501). The apparatus then prepares continuous concentration gradients of either the standard substance or the compound being tested.

If the compound has been categorized as an agonist during the screening mode, the apparatus will measure and register the concentration dependence of cell response (step 503). During step 503, the apparatus will generate continuous experimental activation curves for the activatory compound. From these curves, one can calculate the potency of the compound in terms, for example, of $EC_{50}$ (the effective concentration of an activator which causes 50% of the maximal stimulatory response of the cells) (step 505). This calculation can be performed using well known in the art curve fitting software. In a preferred embodiment this software may be implemented by the graphical software PRISM, manufactured by GraphPad, Inc.

If the compound is determined to be an antagonist during the screening mode, the apparatus will measure and register the concentration dependence of cell response inhibition in the presence of a standard agonist (step 507). During step 507, the apparatus will generate continuous experimental inhibition curves for the antagonist compound taken at constant concentrations of the standard agonist substance. From these curves, one can calculate the potency of the compound in terms, for example, of $IC_{50}$ (the effective concentration of a blocker which causes 50% of the maximal inhibitory response cells) (step 509). The calculation of the $IC_{50}$ valves can also be implemented in a preferred embodiment with the PRISM software package.

If the compound is determined to be an antagonist, the apparatus will also measure and register the concentration dependence of the cell response to a standard agonist substance in the presence of several concentrations of the antagonist compound (step 511). During step 511, the apparatus will generate a series of continuous experimental activation curves for the standard agonist substance taken at different discrete concentrations of the antagonist compound. The apparatus will then calculate the affinity and the potency of the compound in terms, for example, of $pA_2$ values and determine whether the antagonist is competitive or non-competitive (step 513). The $pA_2$ value is proportional to a negative logarithm of the binding constant of a ligand/receptor complex and is a measure of the affmity of the ligand to the receptor: the bigger $pA_2$ value, the higher the compound's affinity to the receptor. Practically, $pA_2$ value can be calculated from the shift of the activation curves in the presence of different concentrations of the antagonist compound and can be implemented by the formula:

$$pA_{2-Log(R-1)}-Log\ B,$$

where R is a ratio of equipotent concentrations of the standard agonist substance measured both in the presence of discrete concentration (B) of the antagonist compound and without the antagonist. In a preferred embodiment the equipotent concentrations of the standard agonist substance can be found from the PRISM software activation curves. With the above sets of experimental curves, one can evaluate the potency and the pharmacological profile for the compound under investigation in accordance with Cheng-Prusoff (Cheng & Prusoff, 1973, incorporated herein by reference), Gaddum (Gaddum, 1957, incorporated herein by reference) or Schild (Arunlakshana & Schild, 1959, incorporated herein by reference) analyses.

A detailed description of the operation of the negative pressure fluidics system of FIG. 3 is given below.

The process is started when a computer prompts an operator to chose a mode of operation from a choice of three modes: system priming mode, screening mode and potency profiling mode. In the presently preferred top-level process, the first choice is to perform system priming. Referring to FIG. 3, before the priming process starts, the operator is prompted to place the nozzles of intake ports 309, 325 and 351 into a reservoir 305 filled with a buffer, the nozzles of the intake ports 336 and 338 into reservoirs 337 and 339, respectively, filled with corresponding calibration solutions, and the nozzle of the intake port 348 into the reservoir 349 filled with a cell suspension.

Figure 6A:
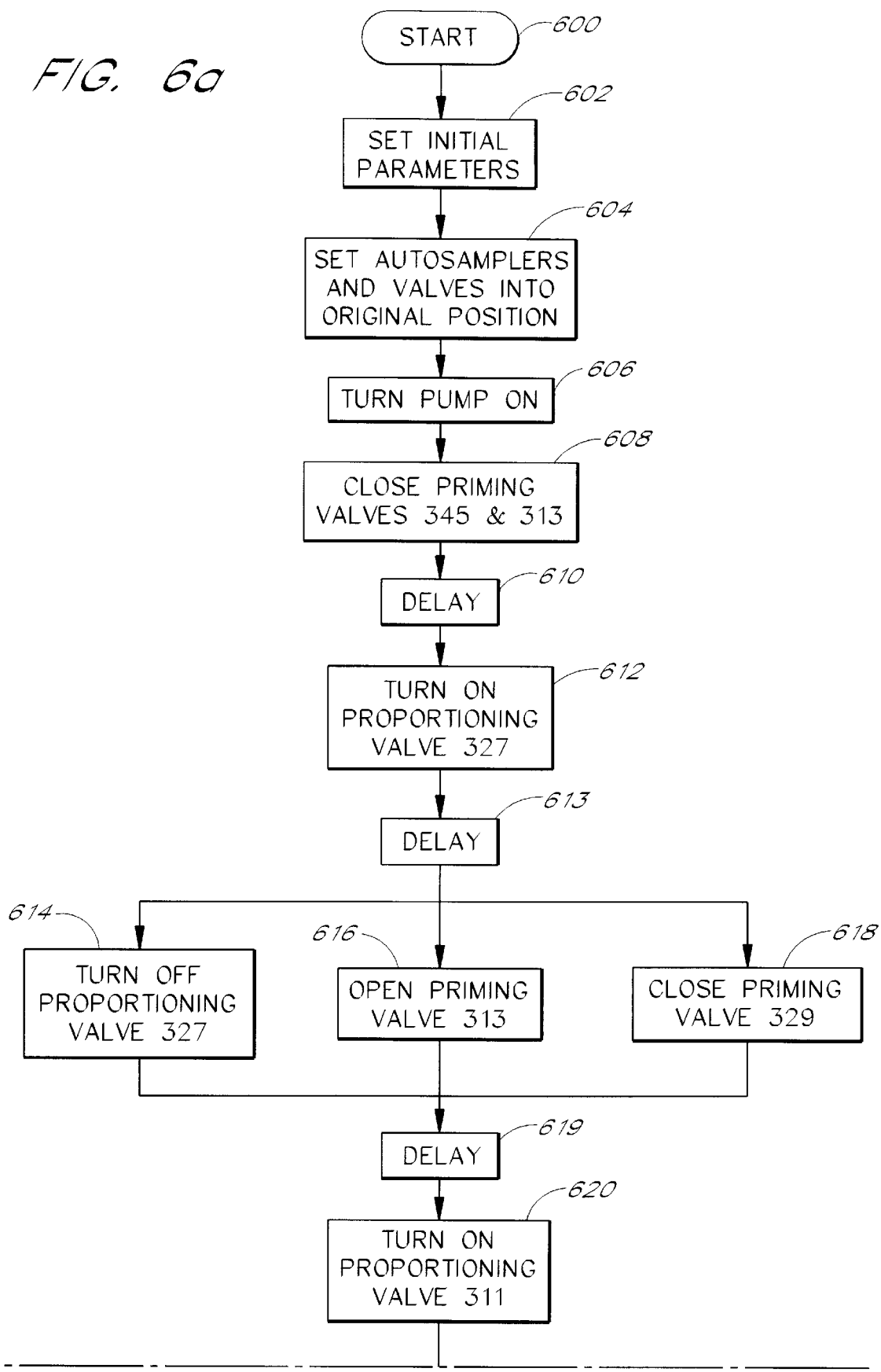
FIG. 6 is a flow diagram of a preferred primary mode operation which may be implemented by a combinatorial screening apparatus of the present invention.
Figure 6B:
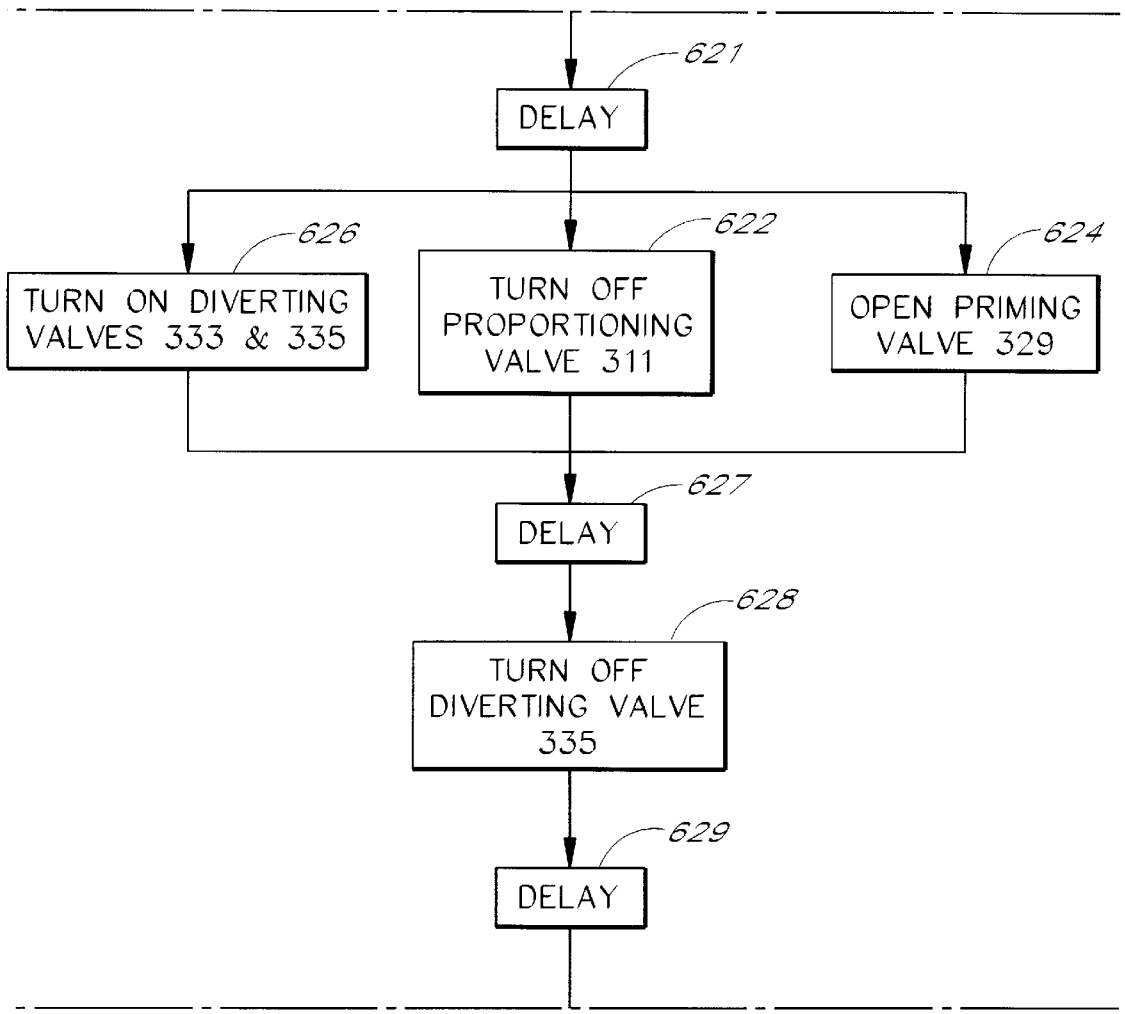
Figure 6C:
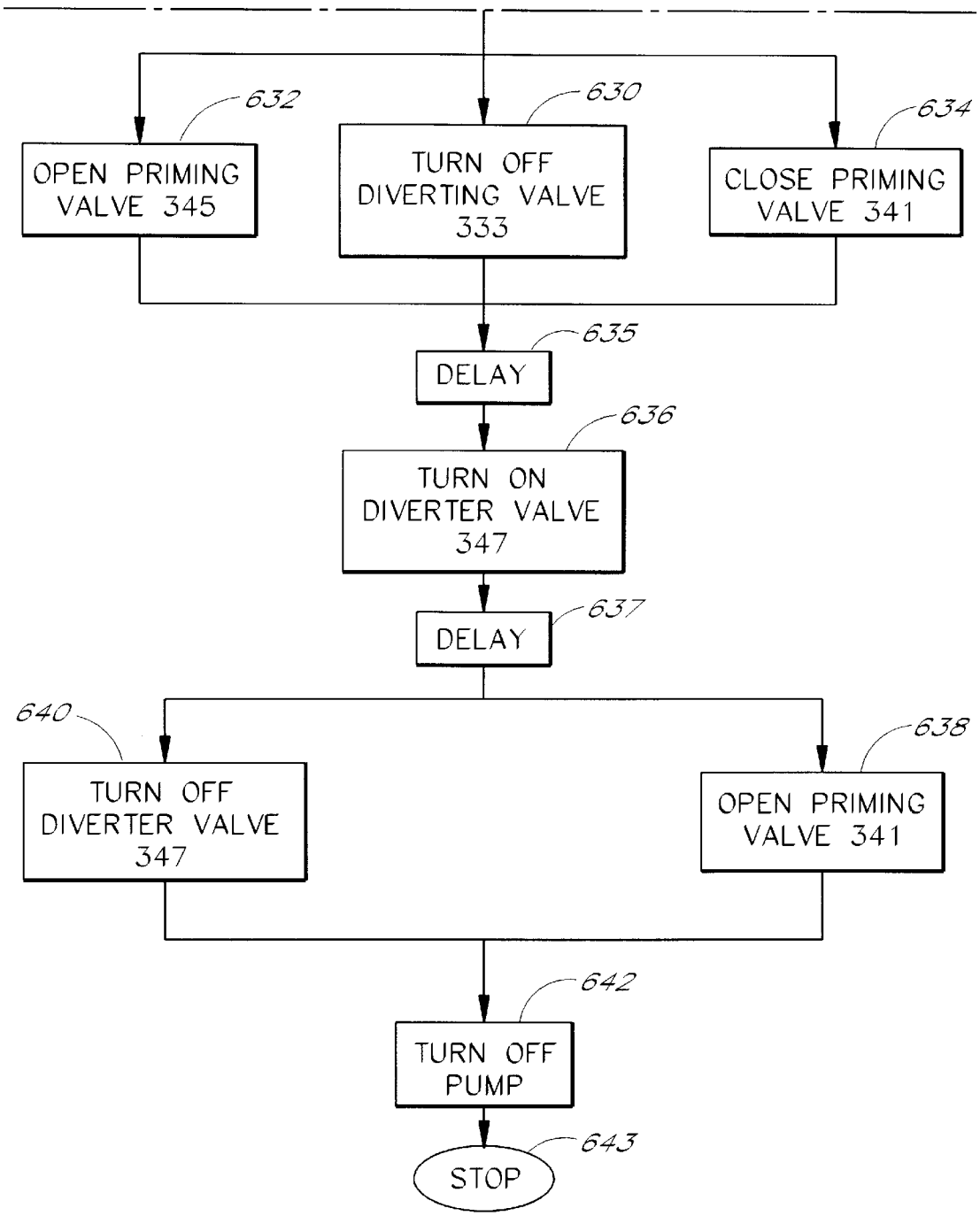
Figure 7B:
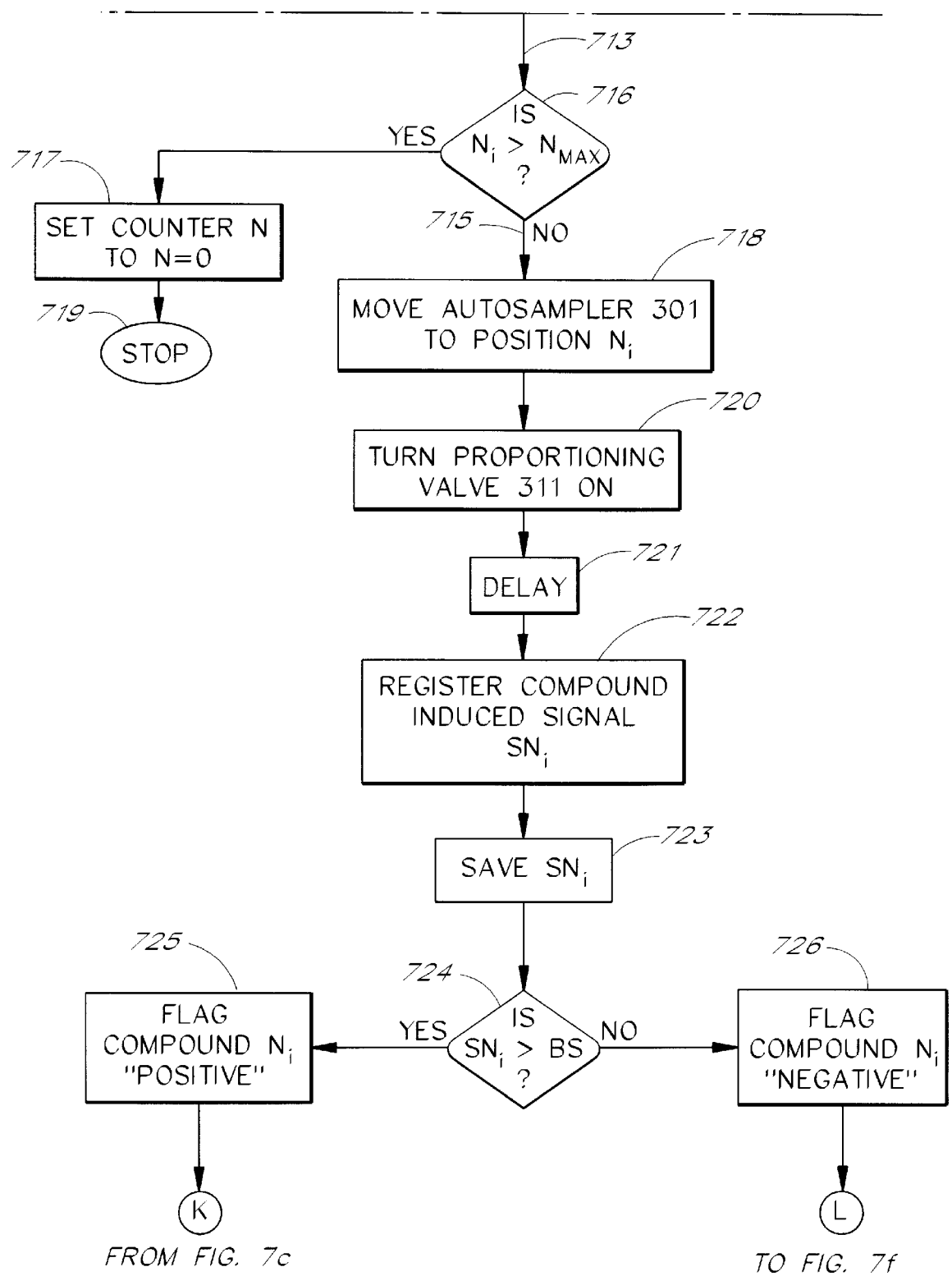
FIG. 7 is a flow diagram of a preferred screening mode operation which may be implemented by a combinatorial screening apparatus of the present invention.
Figure 7C:
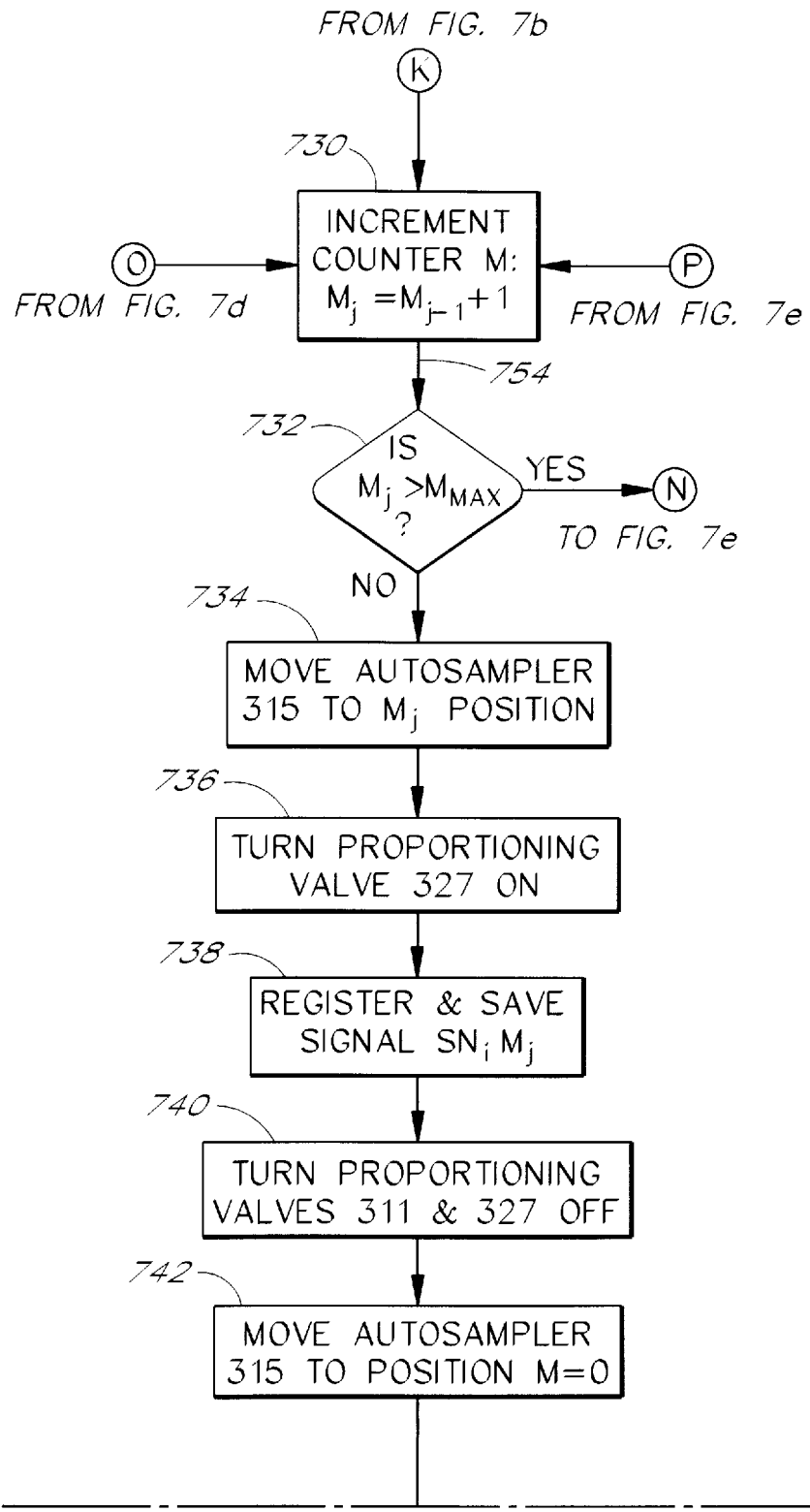
Figure 7D:
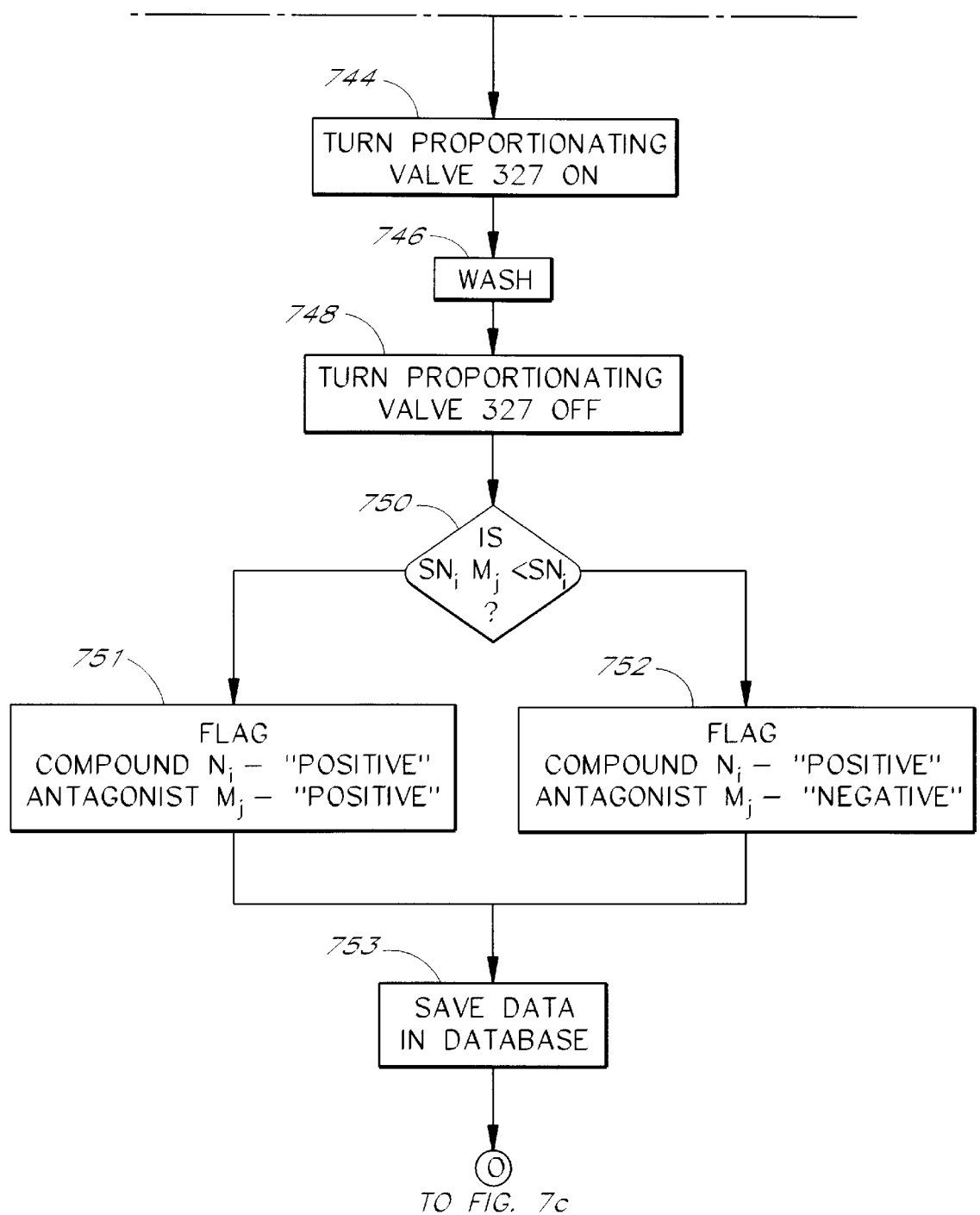
Figure 7E:
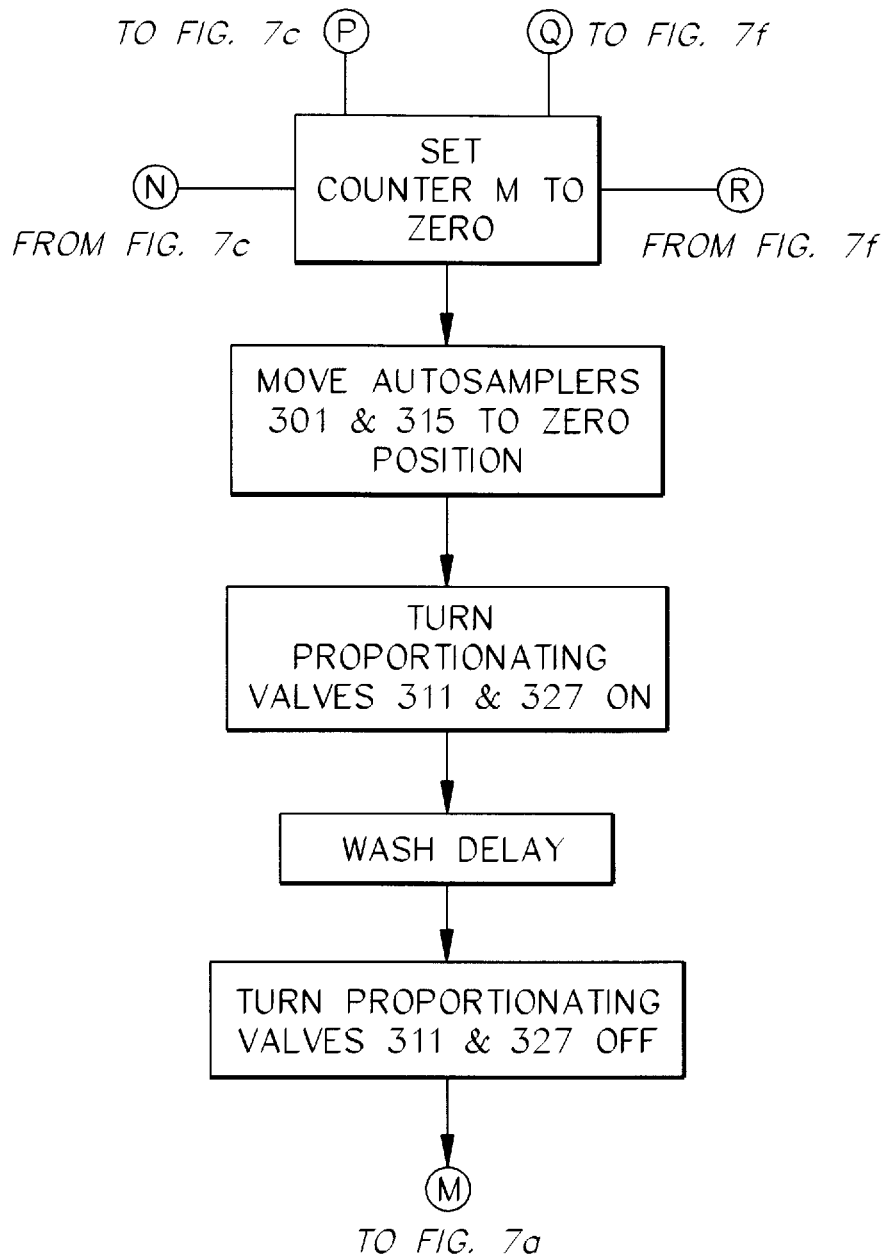
Figure 7F:
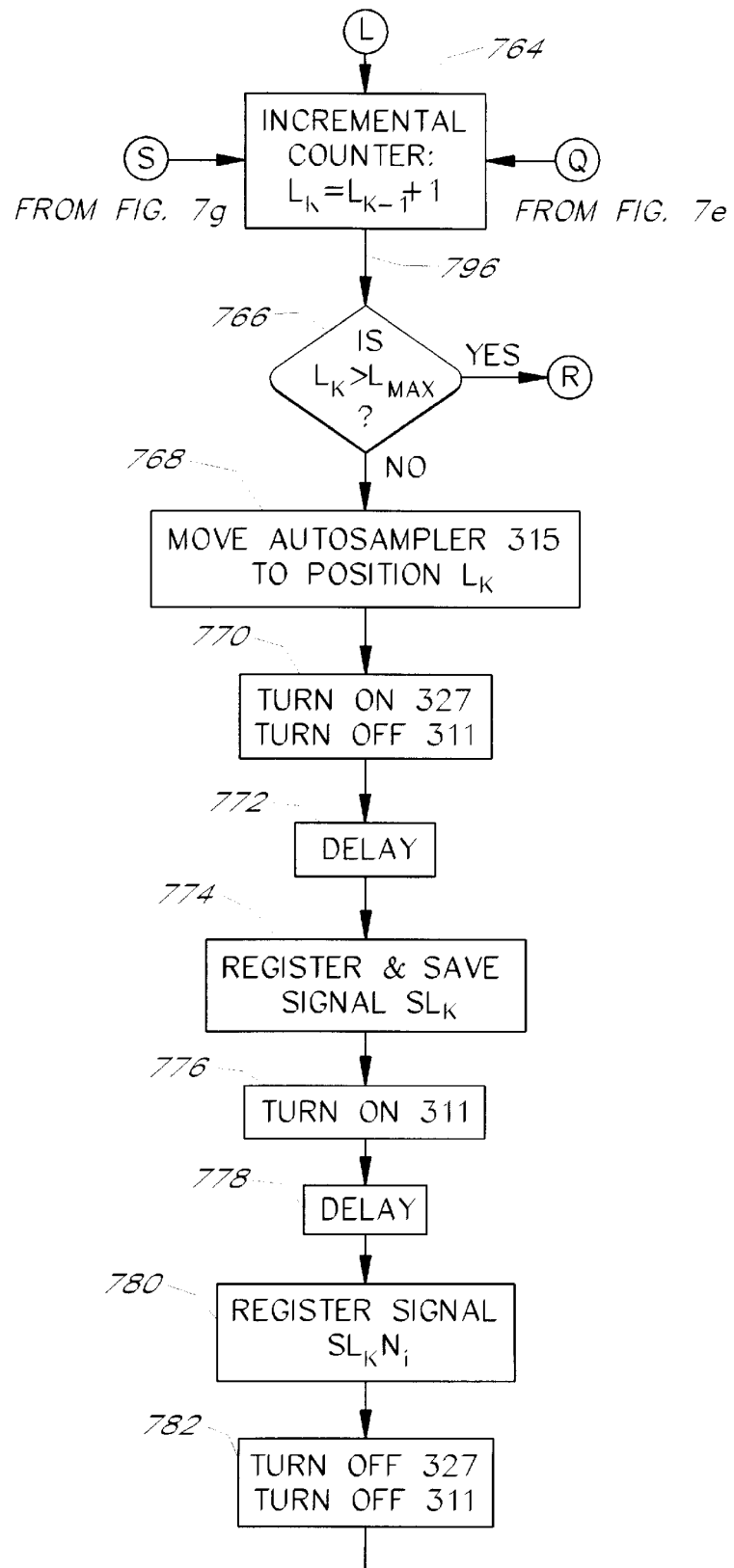
Figure 7G:
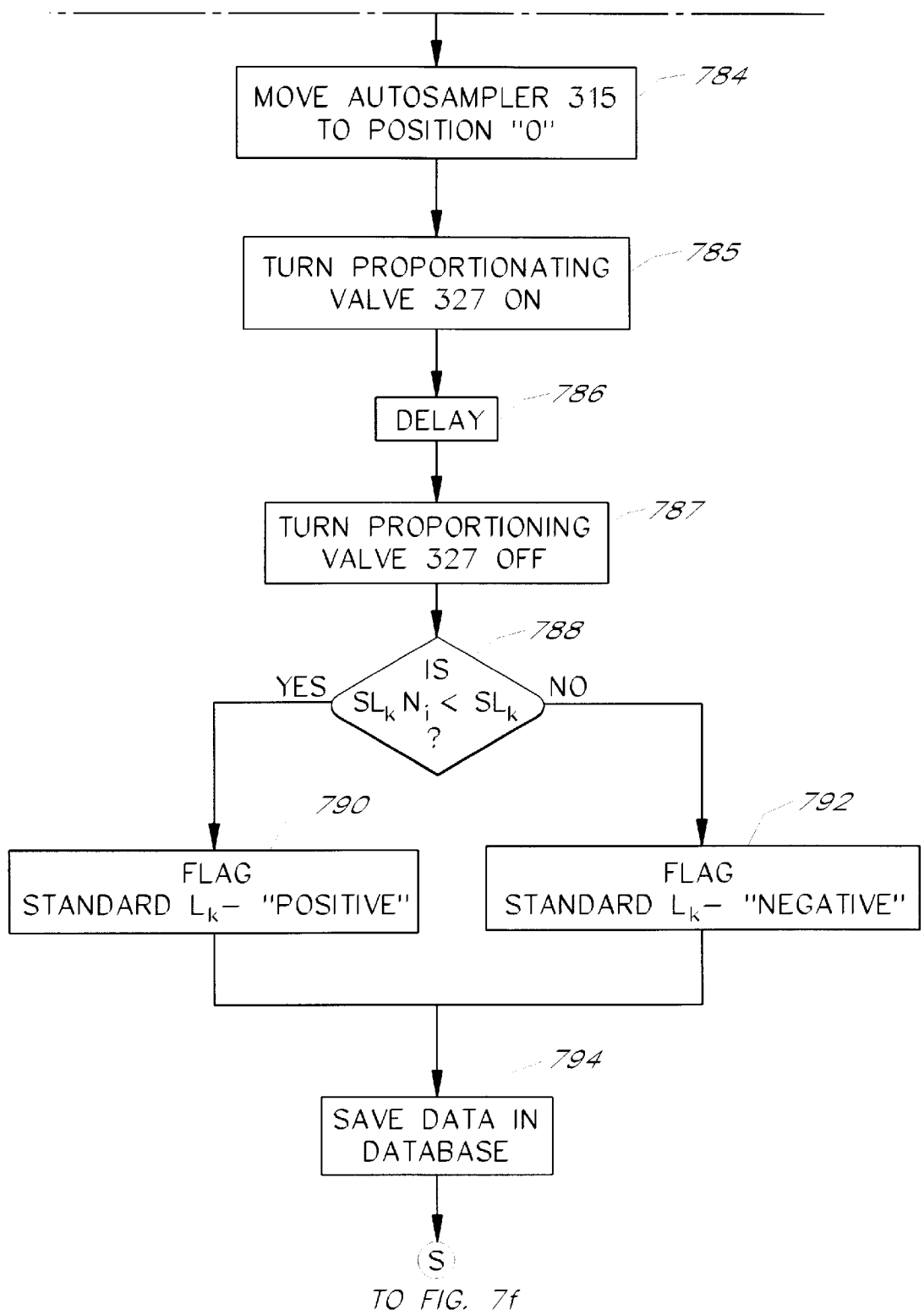
Figure 8A:
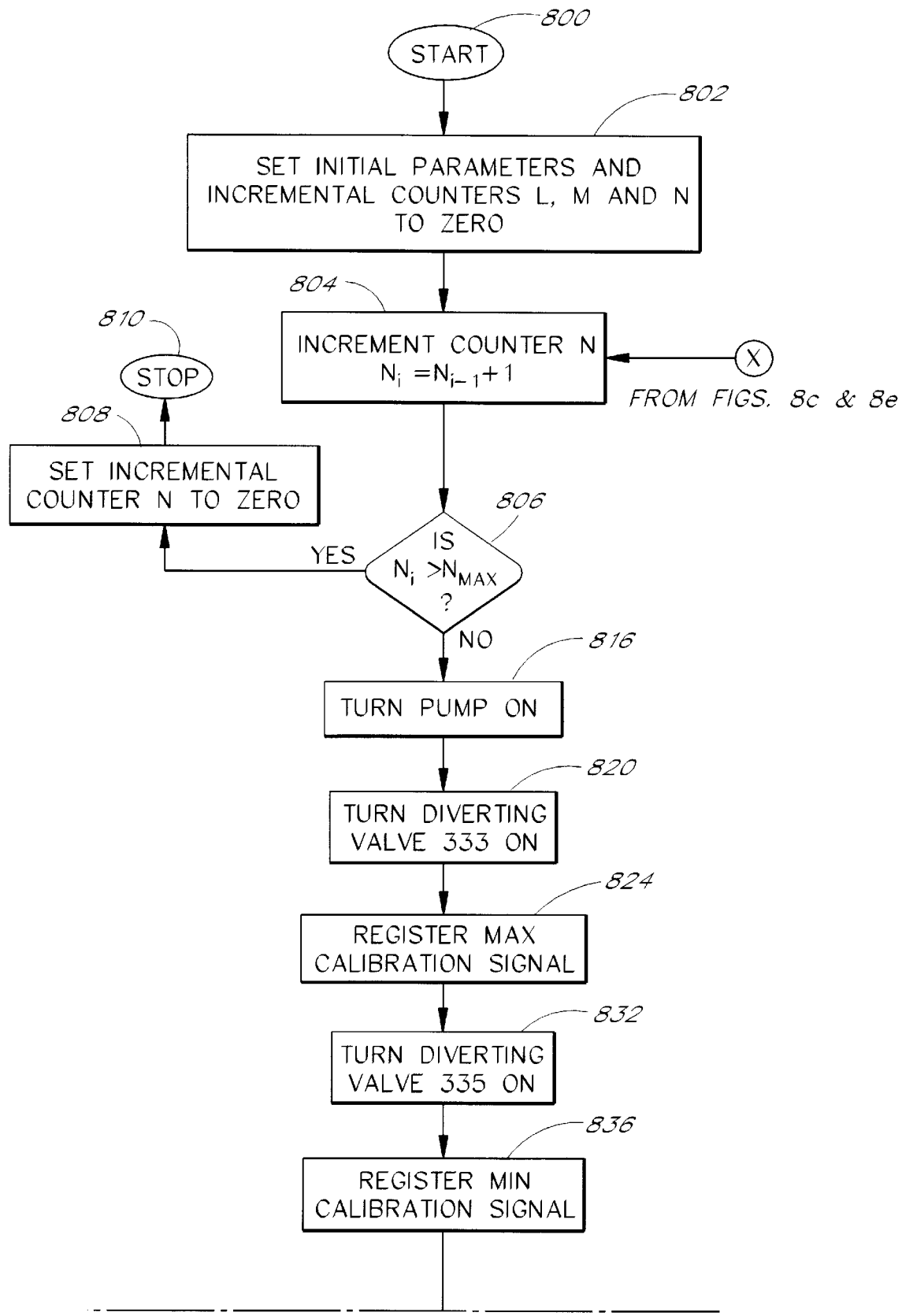
FIG. 8 is a flow diagram of a preferred potency mode operation which may be implemented by a combinatorial screening apparatus of the present invention.
Figure 8B:
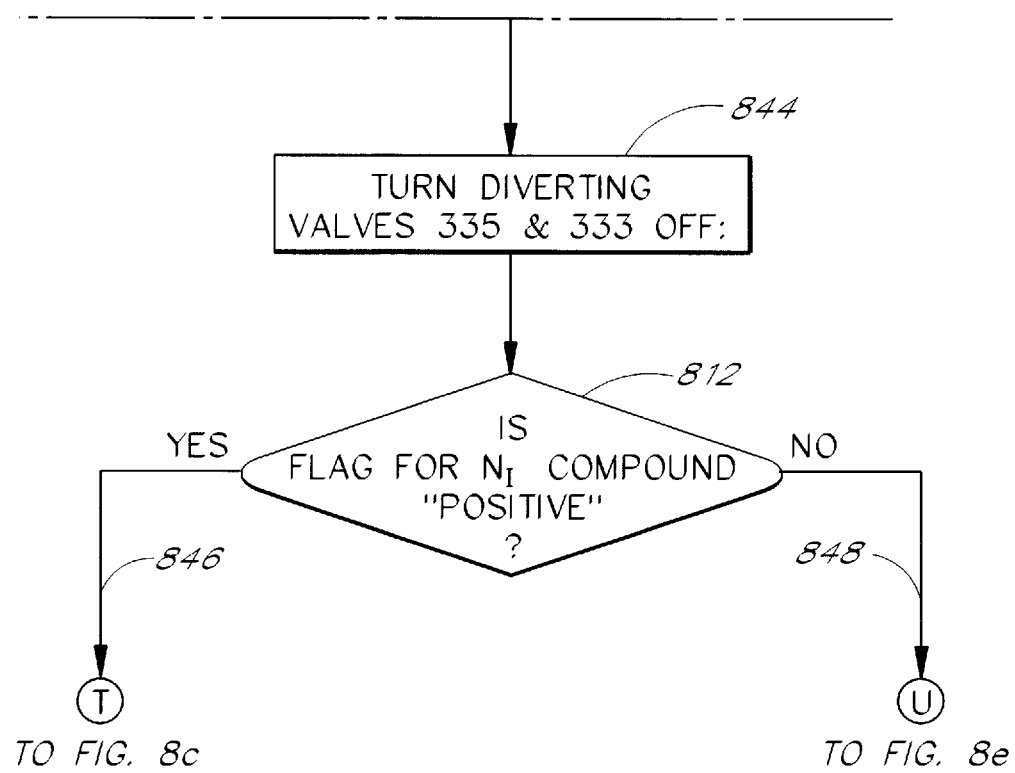
Figure 8C:
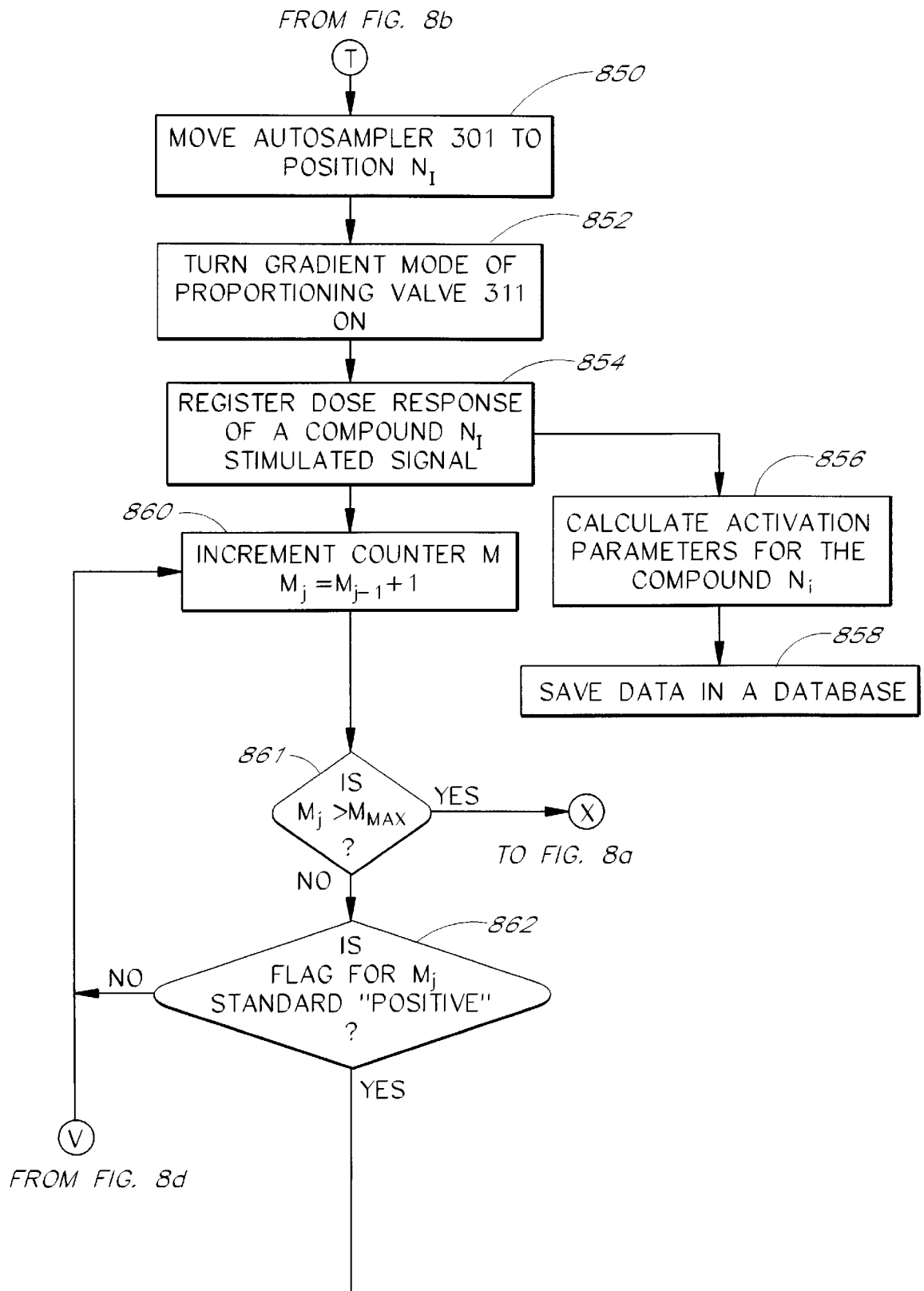
Figure 8D:
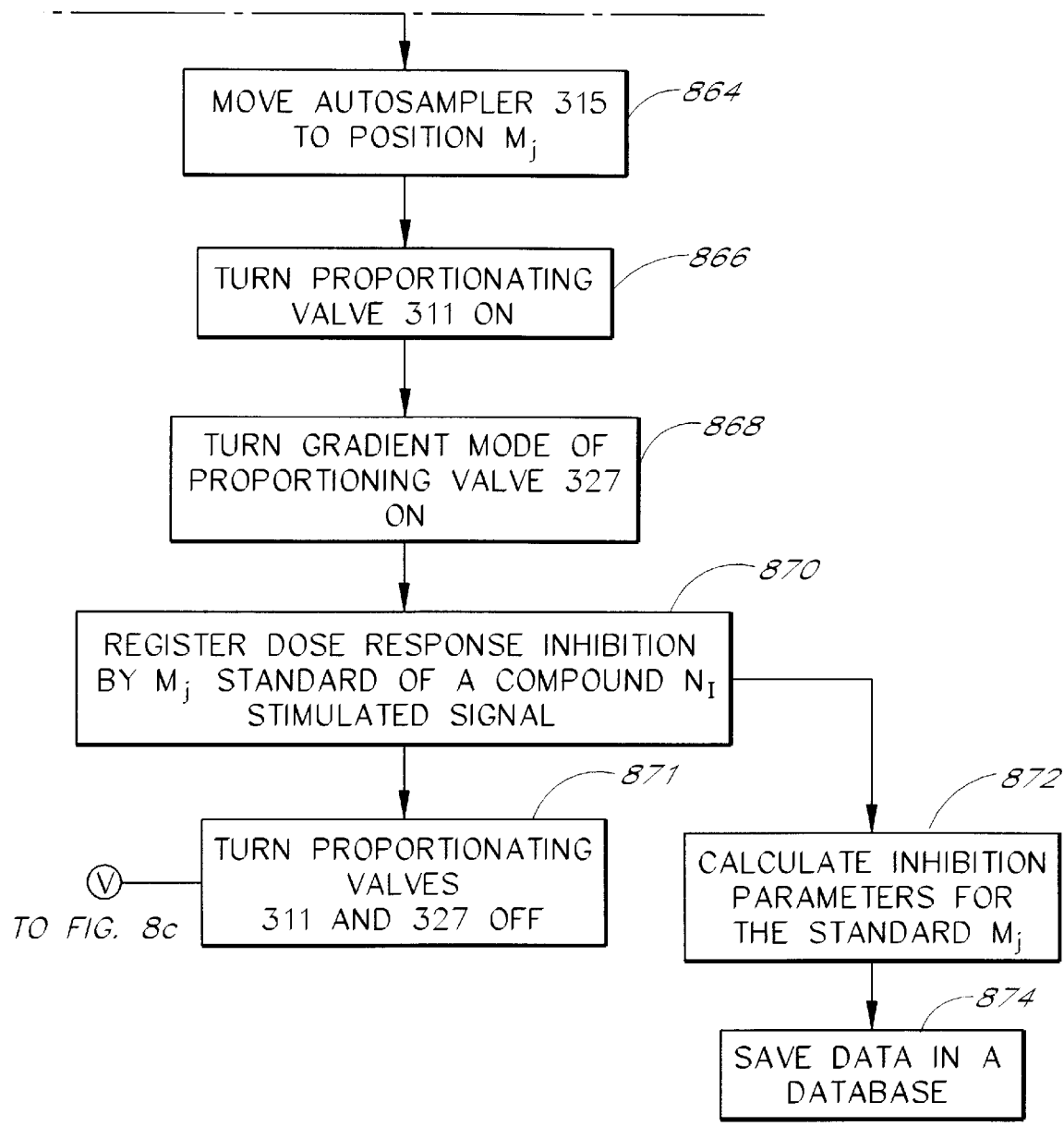
Figure 8E:
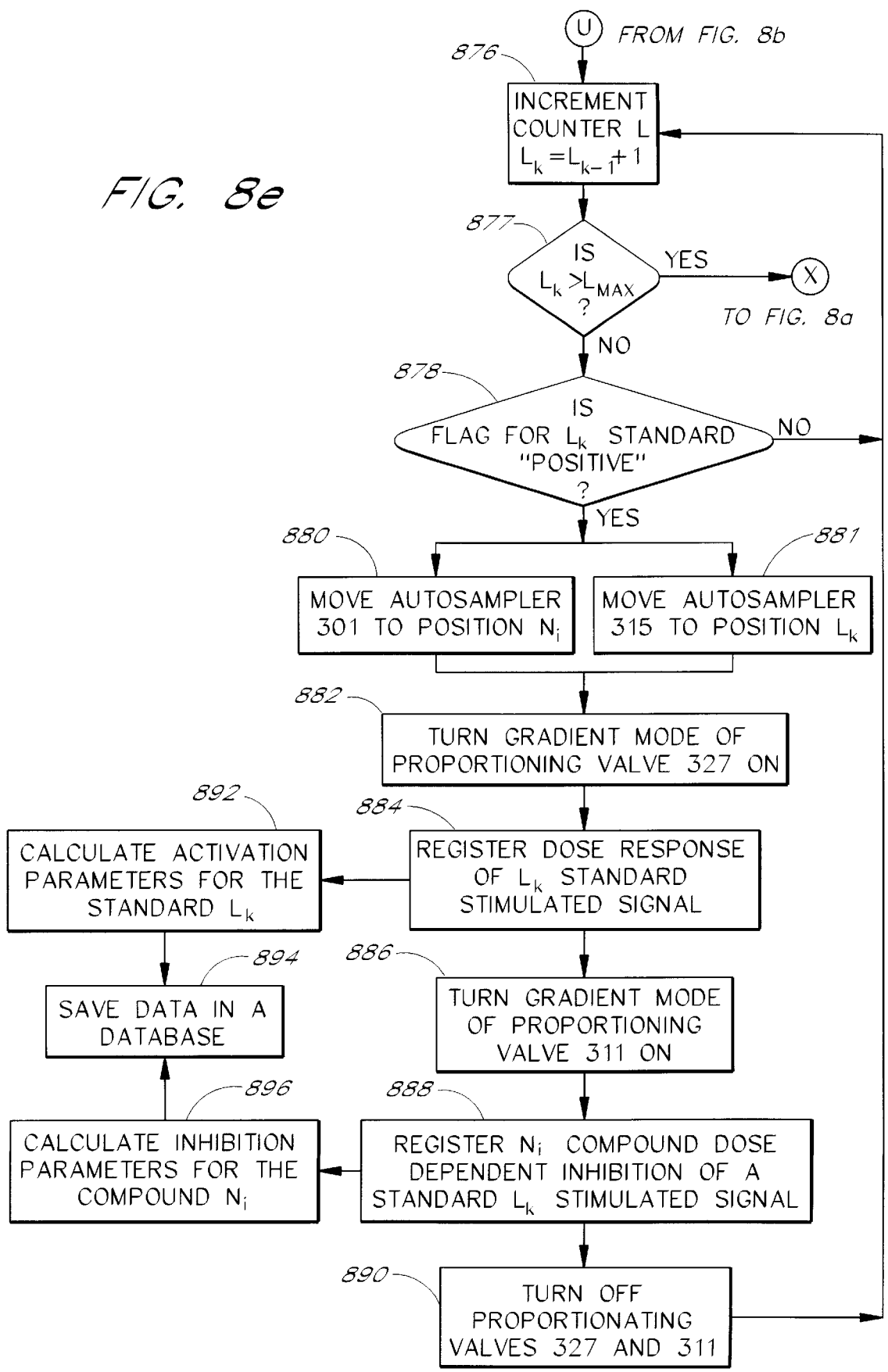

A continuous flow diagram of a preferred system priming process is shown in FIGS. 6a–6d for the preferred negative pressure fluidics system presented in FIG. 3. Referring to FIG. 6a, the system priming program begins from a start state 600 and enters state 602 where it sets all parameters to their initial values. These initial parameters include, but are not limited to, the internal initialization of software variables and subroutines.

Once the initial parameters are determined, autosamplers 301 and 302 (FIG. 3), position their corresponding intake nozzles 307 and 323 at "zero" position (Step 604). Each autosampler, in its "zero" position, contains a reservoir 305 filled with a washing buffer. During step 604, the power supply which supplies power to proportioning valves 311 and 327 (FIG. 3), to diverting valves 333, 335 and 347 (FIG. 3), and to priming valves 313, 329, 341 and 345 (FIG. 3) is turned off. In the preferred embodiment, the priming valves, 313, 329, 341 and 345, are normally opened in a non-powered state (off); the proportioning valves, 311 and 327, in the non-powered (off) state, connect their outlets 312 and 328 with respective "normally opened" intake ports, 309 and 325; and in the non-powered (off) state, the diverting valve 335 connects its common outlet 334 with the "normally opened" intake port 336, diverting valve 333 connects its common outlet 342 with the "normally opened" intake port 332, and diverting valve 347 connects its common outlet 346 with the "normally opened" intake port 348.

After the system has been initialized, peristaltic pump 357 is started (Step 606) and priming valves 313 and 345 are turned on (Step 608). In the powered state, the priming valves 313 and 345 are closed. This forces the buffer flow through tubing 325, outlet tubing 328 of proportioning valve 327, priming valve 329, mixing chamber 331, intake tubing 332 and outlet tubing 342 of the diverting valve 333, priming valve 341, mixing chamber 343, a reaction developing line 353, detector 355, pump 357 and then into a drain container 359.

Referring again to FIG. 1, computer 123 implements software code 125 to provide control signals to a controller 109 which controls the various valves, chambers etc. of the system. This control signal is delayed in order to provide adequate time for liquid to fill the fluidic lines (Step 610). Next, the proportioning valve 327 is turned on (Step 612). While proportioning valve 327 is in the powered state, the buffer located at "zero" position of the autosampler 315 will flow through tubing 323, outlet tubing 328 of proportioning valve 327, priming valve 329, mixing chamber 331, intake tubing 332 and outlet tubing 342 of diverting valve 333, priming valve 341, mixing chamber 343, a reaction developing line 353, detector 355, pump 357 and then into a drain container 359.

After energizing the proportioning valve 327, the control signal is delayed again (Step 613) in order to provide the time needed for the buffer to fill out the fluidics system. After the delay in Step 613, the control signal will set the proportioning valve 327 to its off position (Step 614), turn off (open) priming valve 313 (Step 616) and turn on (close) the priming valve 329 (Step 618). This will fill out fluidic lines 309, 312, 332, 342, priming valve 341, mixing chamber 343, a reaction developing line 353, detector 355 and pump 357 during a delay (Step 619) which is needed for the lines to be filled with buffer 305.

Next, the proportioning valve 311 is powered (Step 620) for a time duration controlled by Step 621. During this delay period, the same fluidic lines are being fed with the buffer located at "zero" position of the autosampler 301, coming through the nozzle 307.

After the delay period (Step 621) the control signal simultaneously turns off both proportioning valve 311 (Step 622) and priming valve 329 (Step 624) and turns on both diverting valve 335 and diverting valve 333 (Step 626). During a delay period, determined by Step 627, the liquid flow will be directed from intake tubing 338 and outlet tubing 334 of the diverting valve 335 through the intake tubing 340 and the outlet tubing 342 of the diverting valve 333 through the priming valve 341, the mixing chamber 343 and further through the reaction developing line 353, the detector 355, the pump 357 and then to the drain container 359. Then the control signal turns off diverting valve 335 (Step 628), which allows the same fluidic lines to be fed from intake tubing 336. The length of time required is a function of the length of the different lines involved and the rate of fluid flow through the system, which for any particular system can be readily determined.

After the delay provided by Step 629, the control signal turns off diverting valve 333 (Step 630), turns off (opens) priming valve 345 (Step 632) and turns on (closes) priming valve 341 (Step 634). Under these conditions, the liquid flow will be directed from the intake tubing 348 to outlet tubing 346 of diverting valve 347, through the priming valve 345, the mixing chamber 343, the reaction developing line 353, the detector 355, the pump 357 and then to the drain container 359. The time required for the above liquid flow to occur is provided by a delay period in Step 635. After this delay, the control signal turns on diverting valve 347 (Step 636), which allows the same fluidic lines to be filled with the buffer 309 coming from tubing 351, during a delay period provided in Step 637.

After the delay provided by Step 637, the control signal turns off (opens) priming valve 341 (Step 638), and turns off the diverting valve 347 (Step 640). The control signal then turns off pump 357 (Step 642). Finally, the priming program ends the system priming mode and all components of the fluidics system are filled with liquids (Step 643).

The state of the valves at each step of the program is shown in FIG. 6d. Priming valves 345, 341, 313 and 329 are of a two-way normally opened type. Diverting valves 335, 333 and 347 are of a three-way type with one common outlet port and one each normally opened and normally closed intake ports. Proportionating valves 311 and 327 are also of the three-way type similar to diverting valves 335, 333 and 347. The symbols "−" and "+" indicate turned off and turned on state of the valves. The state of all the valves after the priming mode is finished is the same as at the initial state.

After the priming of the system is done, the operator is prompted to start either the screening or potency profiling mode. If screening mode is chosen, the operator is prompted to specify how many compounds are located in the set of compounds to be tested, $N_{max}$, and how many antagonists, $M_{max}$, and agonists, $L_{max}$, solutions are located in the respective sets of the standards. If potency profiling mode is chosen, the operator is prompted to specify which compounds in a set should be measured.

A continuous flow diagram of the presently preferred screening mode with the negative pressure fluidics system of FIG. 3 is shown on FIGS. 7a–7g.

The screening program begins from a start state 700 and enters state 702 where it sets all parameters to their initial values. These initial parameters include, but are not limited to, the internal initialization of software variables and subroutines.

Once the initial parameters are determined, the autosamplers 301 and 315 (FIG. 3) position the intake nozzles 307 and 323 at the corresponding "zero" position occupied by a wash buffer reservoir 305 (Step 704), and turns off proportioning valves 311 and 327, diverting valves 333, 335 and 347, and priming valves 313, 329, 341 and 345 (Step 706). In a turned off state, priming valves 313, 329, 341 and 345, are normally opened, proportioning valves 311 and 327 connect, respectively, their outlets 312 and 328 with corresponding "normally opened" intake ports 309 and 325, diverting valve 335 connects its common outlet 334 with "normally opened" intake port 336, diverting valve 333 connects its common outlet 342 with the "normally opened" intake port 332, and diverting valve 347 connects its common outlet 346 with the "normally opened" intake port 348.

After the system has been initialized, pump 357 is started (Step 708). This will force the wash buffer from the "zero" positioned reservoirs of both autosamplers 301 and 315 to run through nozzles 309 and 325 and outlet ports 312 and 328 of proportioning valves 311 and 327, respectively, priming valves 313 and 329, mixing chamber 331, intake port 332 and outlet port 342 of diverting valve 333, priming valve 341, mixing chamber 343, a reaction developing line 353, detector 355, pump 357 and then into a drain container 359. In mixing chamber 343 this flow is mixed with cell suspension 349 coming from intake tubing 348 and an outlet port 346 of diverting valve 347 through priming valve 345. Thus, the total flow passing mixing chamber 343 is a sum of three flows, one of each coming from the proportioning valves 311 and 327 and one coming from diverting valve 347. During this step, both proportioning valves supply wash buffer 305 from the reservoirs located at "zero" position of each autosampler in such a way that the final mixture consists of one part cell suspension 349 and two parts wash buffer 305.

After the delay determined in step 709, which is needed for the flow of the mixture of cell suspension 349 and wash buffer 305 to stabilize, detector 355 registers a basal signal produced by the cells alone, BS (Step 710). After the BS signal is registered, it is saved as a reference (Step 712) and computer 123 (FIG. 1) triggers incremental counter N (Step 714).

The numerical content of the incremental counter N is increased by unity each time it is triggered thus determining the position of the nozzle of intake port 307 of autosampler 301 which samples the sets of compounds 303 to be tested. Next, the numerical content, $N_i$, of the incremental counter is checked against an entered maximum number of the compounds to be tested, $N_{max}$ (Step 716). If $N_i$ does not exceed $N_{max}$, autosampler 301 positions nozzle 307 into the compound reservoir located at the $N_i$ position of a rack of compounds 303. Next, proportioning valve 311 is switched on to open its "normally closed" intake port 307 to the common output port 312 (Step 720). During Step 720, the combined flow in mixing chamber 343 and afterwards in detector 355, is composed of one portion of buffer 305 coming through nozzle 325 of proportioning valve 327, one portion of the compound 303 to be tested coming from nozzle 307 of proportioning valve 311 and one portion of cell suspension 349 coming from the intake tubing 348 which is "normally opened" to the output port 346 of diverting valve 347. After a delay provided by Step 721, which is needed for the mixing process to stabilize, detector 355 registers a signal, $SN_i$, produced by the cells in the presence of the given compound, $N_i$ (Step 722). After the $SN_i$ signal is registered, its value is saved as a reference value (Step 723). The value of the $SN_i$ signal is then compared with the value of the reference basal signal, BS (Step 724). If the $SN_i$ signal is greater than the BS signal, the computer 123 (FIG. 1) will "flag" the corresponding compound as "positive" (Step 725), which means that the compound stimulates the cell signal. If $SN_i$ is greater than BS, the computer 123 controls a set of antagonists and calculates corresponding coordinates for positioning the nozzle 323 of autosampler 315 over the antagonist containing reservoirs located in rack 317. If $SN_i$ is less than BS, computer 123 will "flag" the corresponding compound as "negative" (Step 726). In this case, the computer 123 controls a set of agonists and calculates corresponding coordinates for positioning the nozzle 323 of autosampler 315 over the agonist containing reservoirs located in rack 319.

Each time the condition, "$SN_i > BS$", is satisfied, the program flow will go through loop K–O of the incremental counter M (Step 730). The incremental counter, M, increases the count number by one each time it is triggered and thus determines the successive positions of nozzle 323 of autosampler 315 which serves the set of standard antagonists located on rack 317. Next, computer 123 checks if the numerical content of the incremental counter ($M_j$) exceeds the maximun number of standards to be tested ($M_{max}$) entered by the operator (Step 732).

If $M_j$ is less than or equal to $M_{max}$, autosampler will position nozzle 323 into the standard antagonist reservoir, located on rack 317 corresponding to the numerical content of the incremental counter, $M_j$ (Step 734). Next, proportioning valve 327 is switched over to connect its "normally closed" intake port 323 with the outlet port 328 (Step 736). During Step 736, the combined flow through mixing chamber 343, reaction developing lines 353 and detector 355 is composed of one portion of standard antagonist coming from proportioning valve 327, one portion of the compound to be tested, coming from proportioning valve 311 and one portion of the cell suspension coming from diverting valve 347.

Next, detector 355 registers and saves (Step 738) for further comparison, a signal, $SN_iM_j$, produced by a given compound, $N_i$, in the presence of a given standard antagonist, $M_j$. Then, both proportioning valves 311 and 327 are turned off (step 740). This closes intake ports 307 and 323 and opens intake ports 309 and 325 to the corresponding outlet ports 312 and 328. Autosampler 315 then positions nozzle 323 into "zero" position occupied by wash buffer reservoir 305. The proportioning valve 327 is then turned on again to open its "normally closed" intake port 323 into the outlet port 328 (Step 744) and the content of nozzle 323 is washed out (Step 746). Next, proportioning valve 327 is turned off to close intake port 323 and to open "normally opened" intake port 325. During this process, the fluidic lines are washed with buffer coming from nozzle 325 of autosampler 315.

Next, Computer 123 (FIG. 1) compares signal, $SN_i$, measured in the presence of a compound $N_i$ alone, with the signal, $SN_iM_j$, measured in the presence of both a compound $N_i$ and a standard antagonist, $M_j$ (Step 750). If the signal in the presence of a standard antagonist, $M_j$, is lower than the signal generated by a compound $N_i$ alone, $SN_iM_j<SN_i$, then both the compound $N_i$ and the standard antagonist, $M_j$, is flagged as "positive" (Step 751). If both signals are equal to each other, then the compound $N_i$ is flagged as "positive" and the standard antagonist $M_j$ is flagged as "negative" (Step 752). After the data is flagged, the data, containing the ID number of the compound $N_i$ with its flag value and ID number of the standard antagonist $M_j$ with its flag value is transferred into a database (Step 753). After the data is saved the program loops back to trigger the incremental counter M (Step 730), to increase its count by one and Step 754 is repeated until the condition 732 is achieved.

When the condition determined in the decision step 732 is met, that is the compound has been tested against all standard antagonists in a given set, the program resets the content of incremental counter M to zero (Step 755), and both autosampler 301 and autosampler 315 position their respective nozzles 307 and 323 to "zero" position, where the reservoirs with a washing buffer 305 are located (Step 756). Next, both proportioning valves 311 and 327 are turned on (Step 758). This opens "normally closed" intake ports 307 and 323 to the corresponding outlet ports 312 and 328. During this washing delay period determined by Step 760, the contents of both nozzle 312 and nozzle 328 are washed out with buffer 305. After Step 760 is finished, both proportioning valves 311 and 327 are turned off (Step 762). After the washing delay period (Step 760), the program loops back to the incremental counter N content of which is incremented by one (Step 714) by triggering signal $S_{tr}$ from the computer 123 (FIG. 1). Then, the numerical content $N_i$ of counter N is compared with the maximum number, $N_{max}$, of the compounds to be tested. If $N_i$ exceeds $N_{max}$, the content of incremental counter N is zeroed (Step 717) and the screening mode is stopped (Step 719). Otherwise, Step 715 will be repeated with the next compound.

If the condition of the decision process 724, $SN_i>BS$, is not satisfied, the $N_i$ compound is flagged as "negative" (Step 726) and the incremental counter L is triggered (Step 764). The incremental counter L is increased by one (Step 764) each time it is triggered and thus determines the successive positions of nozzle 323 of autosampler 315 relative to the set of standard agonists located on rack 319. Next, the numerical content, $L_k$, of incremental counter L is compared with the maximum number, $L_{max}$, of standard agonists to be used (step 766).

If $L_k$ is less than or equal to the $L_{max}$, autosampler 315 positions nozzle 323 into the standard agonist reservoir in rack 319, which corresponds to the numerical content, $L_k$, of incremental counter L. Next, proportioning valve 327 is turned on to open its "normally closed" intake port 323 to outlet port 328 and proportioning valve 311 is turned off to close its intake port 307 and open intake port 309 to outlet port 312 (Step 770). During step 770, the combined flow coming through mixing chamber 343, reaction developing lines 353 and detector 355 is composed of one portion of standard agonist 319 coming from inlet port 323 of proportioning valve 327, one portion of buffer 305, coming from inlet port 309 of proportioning valve 311 and one portion of cell suspension 349 coming from the diverting valve 347.

After a delay period provided by Step 772, which is needed for the mixing process to stabilize, a signal, $SL_k$, produced by a given standard agonist, $L_k$ is registered and saved (Step 774). Next, proportioning valve 311 is turned on to open its "normally closed" intake port 307 to outlet port 312 (Step 776). A delay period needed for the mixing process to stabilize is provided in Step 778, after which a signal, $SL_kN_i$, is stimulated by a given standard agonist, $L_k$, in the presence of a given compound, $N_i$ is registered and saved in (Step 780).

After the signal $SL_kN_i$, is registered (Step 780), both proportioning valves 311 and 327 are turned off to close their respective "normally closed" intake ports 307 and 323 and to open intake ports 309 and 325 to the corresponding outlet ports 312 and 328 (Step 782). Next, autosampler 315 positions the nozzle of intake port 323 to its "zero" position which corresponds to washing buffer reservoir 305 (Step 784). Then, the proportioning valve 327 is turned on (Step 785). This opens the "normally closed" intake port 323 to the outflow port 328, and after some delay provided by step 786, which is needed for washing out the content of nozzle 323, the proportioning valve 327 is turned off (Step 787), and the two signals, $SL_kN_i$ and $SL_k$, are compared (Step 788).

If $SL_kN_i$ is less than $SL_k$, then the corresponding standard agonist, $L_k$, is flagged as "positive" (Step 790). If both signals are equal to each other, then the standard agonist, $L_k$, is flagged as "negative" (Step 792). After the data is flagged, the data, containing the ID number of the compound $N_i$ with its flag value and the ID number of the standard agonist $L_k$ with its flag value is transferred into a database (Step 794). After the data is saved the program triggers the incremental counter L (Step 764) to increase its count by one and Step 796 is repeated until condition 766 is achieved.

When the condition determined in Step 766 is met, that is the compound has been tested against all standard agonists in a given set, the content of incremental counter L is reset to zero (Step 755) and both autosampler 301 and autosampler 315 position their respective nozzles 307 and 323 to "zero" position where the reservoirs with washing buffer 305 are located (Step 756). The system then turns on both proportioning valve 311 and proportioning valve 327 to open "normally closed" intake ports 307 and 323 to the corresponding outlet ports 312 and 328 respectively (Step 758). During a washing period provided by Step 760, the contents of both nozzle 307 and nozzle 323 are washed out with the buffer 305. Next, both proportioning valves 311 and 327 are turned off (Step 762) and incremental counter N is incremented by one (Step 714). Next, the new triggered numerical content $N_i$ of the incremental counter N is compared with the maximum number, $N_{max}$, of compounds to be tested (Step 716). If $N_i$, exceeds $N_{max}$, the counter N is set to zero in step 717 and the screening mode is stopped (Step 719). Otherwise, the whole cycle will be repeated with a subsequent compound.

After the screening mode is stopped (Step 719), the operator is prompted by the computer to choose either potency profiling mode or to repeat screening mode with a new set of compounds.

A continuous flow diagram of the presently preferred potency profiling mode with the negative pressure fluidics system of FIG. 3 is shown in FIGS. 8a–8e.

The potency profiling program begins from a start state 800 and enters state 802 where it sets all incremental counters, L, M, and N, to zero and sets all parameters to their initial values. This initial parameters include, but are not limited to, the internal initialization of hardware and software variables and subroutines. Next, the incremental counter N is started (Step 804), and its numerical content, $N_i$, is compared with the maximum number, $N_{max}$, of standards, entered by the operator before starting the program (Step 806). If $N_i$ exceeds $N_{max}$, the incremental counter N is zeroed (Step 808), and the program stops (Step 810). Otherwise, the program will proceed by turning on pump 357 (Step 816). At this point, in accordance with initial parameters setup in Step 802, the nozzles 307 and 323 of autosamplers 301 and 315 are in zero position, proportioning valves 311 and 327, priming valves 313, 329, 341, and 345, and diverting valves 335, 333, and 347 are turned off. During step 816, the combined flow coming through mixing chamber 343, reaction developing lines 353 and detector 355 is composed of one portion of buffer 305 coming from inlet port 309 of proportioning valve 311, one portion of buffer 305, coming from inlet port 325 of proportioning valve 327 and one portion of cell suspension 349 coming from the diverting valve 347. Next, diverting valve 333 is turned on (Step 820), opening "normally closed" intake port 340 into outlet port 342. During this process, the calibration max solution 337, which determines maximum response, flows through tubing 336 which is connected to outlet tubing 334 of diverting valve 335, through intake port 340 of diverting valve 333, through priming valve 341 and then into mixing chamber 343, where it is mixed with cells coming from cell suspension 349, through intake tube 348 and outlet tube 346 of diverting valve 347, and then through priming valve 345 into the mixing chamber 343. The cells calibration max mixture will then flow to developing lines 353, and then to detector 355. Next, the maximum signal is measured and registered (Step 824). Diverting valve 335 is then turned on (Step 832) which opens the "normally closed" intake port 338 to outlet port 334 which allows a calibration min solution 339 to flow through diverting valve 333, priming valve 341 and into mixing chamber 343 where it is mixed with cells coming from cell suspension 349, through intake tube 348 and outlet tube 346 of diverting valve 347, and then through priming valve 345, into mixing chamber 343. The cells/calibration min. mixture then flows to developing lines 353 and then to detector 335. The minimal response signal is then measured and registered (step 836). Next, both diverting valves 335 and 333 are turned off (Step 844). During step 844, the combined flow coming through mixing chamber 343, reaction developing lines 353 and detector 355 is composed of one portion of buffer 305 coming from inlet port 309 of proportioning valve 311, one portion of buffer 305, coming from inlet port 325 of proportioning valve 327 and one portion of cell suspension 349 coming from the diverting valve 347. This is needed to wash out the remains of calibration solution from the fluidics line. Next, the "flag" value of the compound, $N_i$, is checked (Step 812).

If the "flag" value of the $N_i$ compound is "positive", then the system will go to step 850, otherwise it will go to step 876. If the "flag" value of the $N_i$ compound is "positive", autosampler 301 will position nozzle 307 into a reservoir corresponding to the $N_i$ compound, located on rack 303 (Step 850). Next, proportioning valve 311 is operated in a gradient mode (step 852). In the gradient mode, the proportioning valve, 311, combines flows from two intake ports, 307 and 309, in such a way that the proportion of a $N_i$ compound flow and a buffer flow in an outlet port, 312, changes in time to create a discontinuous change of the compound concentration. While the concentration is being changed in time, the fresh portions of the cells, coming into the mixing chamber 313 from the cell suspension 349, at any given time will react with the different concentrations of the $N_i$ compound. The resulting dose response dependence of the signal is registered in Step 854 with the subsequent calculation of the activation parameters for the $N_i$ compound in Step 856 and then saving the data in a database (Step 858).

Next, an incremental counter of the standard antagonists, M, is started (Step 860) and the numerical content, $M_j$, of the counter M is compared with the maximum value, $M_{max}$, entered by the operator (Step 861). If the numerical value $M_j$ does not exceed $M_{max}$, then the "flag" value of the $M_j$ standard is checked (Step 862). If the "flag" value of the $M_j$ standard is not "positive", the incremental counter, M, is increased by one (Step 860), and the steps following Step 860 will be repeated as described above. If the "flag" value of the $M_j$ standard is "positive", autosampler 315 positions nozzle 323 into the reservoir corresponding to the $M_j$ standard antagonist, located on rack 317 (Step 864). After nozzle 323 is immersed into the standard solution, proportioning valve 311 is turned on (Step 866). When the proportioning valve 311 is turned on, it opens its "normally closed" intake port 307 which is immersed, in Step 850, into a reservoir corresponding to the compound $N_i$, so that the $N_i$ compound flows through the fluidics system and generates a signal when it is mixed with the cells 349, coming through intake tubing 348 and outlet tubing of diverting valve 347, priming valve 345 to mixing chamber 343 and further to developing line 353 and detector 355. Next, proportioning valve 327 is operated in a concentration gradient mode (Step 868). In the gradient mode, proportioning valve 327 combines flows coming from the two intake ports, 323 and 325 into outlet port 328 in such a way that the proportion of a $M_j$ standard antagonist flow and a buffer flow changes in time to create a discontinuous change of the standard antagonist concentration. While the concentration is being changed in time, the fresh portions of the cells flow into mixing chamber 343 from cell suspension 349 and react with the mixture composed of the $N_i$ compound at constant concentration and the standard antagonist $M_j$ at the concentration different at any given time. The resulting dose response inhibition by the $M_j$ standard antagonist of the $N_i$ compound stimulated signal is registered in Step 870, with the subsequent calculation of the inhibition parameters for the $M_j$ standard antagonist in a Step 872 and saving the data in a database (Step 874).

After the curve is registered in Step 870 both proportioning valves 311 and 327 are closed (Step 871) and the program flow returns to Step 860 where incremental counter M is incremented by one and the program returns to Step 861 where $M_j$ is compared to $M_{max}$.

When all of the standard antagonists $M_j$ are counted and those with "positive flags" are measured, the numerical value $M_j$ becomes greater than $M_{max}$, and the decision process in Step 861 returns to Step 804 where the incremental counter N increases its numeric value by one. The value of $N_i$ is then compared to $N_{max}$, the maximum number of compounds to be tested (Step 806). If $N_i$ exceeds $N_{max}$, the incremental counter N is reset to zero (Step 808), and the program stops (Step 810).

If, in Step 812, the flag value of the $N_i$ compound is determined to be "negative", a incremental counter L which counts the standards, $L_k$, in a set of agonists, located in rack 319, is updated (Step 876). Next, the numerical value $L_k$ is compared with the maximum number, $L_{max}$, of standard agonists entered by an operator (Step 877).

Until the numerical value $L_k$ of the L counter is greater than the $L_{max}$ value, the program will go to Step 878, where the "flagged" value of the $L_k$ standard is checked. If the flag value is not positive, the program returns to Step 876. If the flag value of the $L_k$ standard is positive, autosampler 301 positions its nozzle 307 into a corresponding reservoir containing the $N_i$ compound located in rack 303 (Step 880), autosampler 315 positions its nozzle 323 into a corresponding reservoir containing the $L_k$ standard agonist, located in rack 319 (Step 881).

Next, the concentration gradient mode of proportioning valve 327 is activated (Step 882) and a dose response stimulation of a signal with the $L_k$ standard agonist is then registered (step 884). In the gradient mode, proportioning valve 327 combines flows coming from the two intake ports, 323 and 325, into outlet port 328 in such a way that the proportion of a $L_k$ standard agonist flow and a buffer flow changes in time to create a concentration gradient of the standard agonist. While the gradient is being created in time, fresh cells flow into mixing chamber 343 from cell suspension 349 through "normally opened" intake tubing 348 and outlet port 346 diverting valve 347, "normally opened" priming valve 345, and discontinuously react with the standard agonist $L_k$ at the discontinuously changing concentration of the standard. Once the dose dependence of the signal stimulation by the $L_k$ standard agonist is registered (Step 884), the activation parameters are calculated (Step 892) and then saved in a database (Step 894).

After the gradient mode of proportioning valve 327 is finished, the valve stays either at the proportion rate reached by the end of the gradient mode or at predetermined proportion rate which establishes the constant concentration of the $L_k$ standard agonist which will be used in further steps. Next, the concentration gradient mode of proportioning valve 311 is activated (Step 886). A dose response inhibition by the $N_i$ compound of the $L_k$ standard agonist stimulated signal is then registered (Step 888) with a subsequent calculation of the inhibition parameters in Step 896. this data is then saved in a database (Step 894). When the registration of the concentration dependence is finished both proportioning valves 311 and 327 are turned off (Step 890) to close their intake ports 307 and 323 and to open "normally opened" intake ports 309 and 325. During this process, the fluidics lines are washed with buffer 305 coming from nozzles 309 and 325 of autosamplers 301 and 315 through outlet ports 312 and 328 of proportioning valves 311 and 327, priming valves 313 and 329, mixing chamber 331, "normally opened" intake port 332 and outlet port 342 of diverting valve 333, "normally opened" priming valve 341, mixing chamber 343, developing line 353 and detector 355. Next, the program returns to Step 876, at which point the above cycle is repeated until all the standard agonists are counted, and those with a positive flag are measured, and the numerical value $L_k$ of the incremental counter becomes greater than the $L_{max}$ value, at which point, the program will return to Step 804.

When all of the compounds $N_i$ are counted (Step 804) and tested, the $N_i$ number becomes greater than the $N_{max}$ value and the incremental counter N is reset to zero (Step 808) and the program stops (Step 810).

Cells for use in the apparatus can be selected for the presence of particular known receptors or for their ability to provide predetermined cellular responses to particular stimuli. A large number of such cells are known. For example, to measure the effect of compounds on calcium mobilization induced by different types of receptors, one may wish to use Jurkat T Cells, Platelets, Umbilical Vein, Endothelial Cells, or Chines Hamster Lung Fibroblasts for thrombin receptor; Cerebellar Purkinje Cells, Cortical Astrocytes and Cortical Glial cells for AMPA receptors; Hippocampal Neurons for NMDA Receptor; P-12 cells for Purinergic Receptors; Oligodendrocytes for Platelet-Derived Growth Factor Receptor, Human Neuroblastoma cells and Pituitary Cells for Neuropeptide Y Receptors and proteintyrosine kinase and proteintyrosine phosphatase receptors; Human Medulloblastoma cells for Endothelin Receptor; Neutrophils for TNFa Receptor; NG108-15 cells for opioid, bradykainin and ATP; Synovial Fibroblasts for Plasminogen Receptors and so on. If one wishes to measure an intracellular ion concentration, for example, one can preincubate the cells with a dye or other detectable material having sensitivity to concentration of that particular ion. (An actual working example illustrating preparation of cells for detection of calcium ion is set forth in Example 1.)

Alternatively, if one wishes to determine the pattern of natural expression of receptors responsible for $Ca^{2+}$ signaling pathway, then one may use the cells of particular interest and then using a set of agonists known to exert their activity through $Ca^{2+}$ mobilization, to characterize the cells by what type of the receptors are expressed in these particular cells. This set of agonists may consist of acetylcholin, adrenaline, noradrenaline, 5-hydroxitriptamine, DOPA, NMDA, AMPA, Angiotensin II, Bradykinin, Bombesin, Opioid, Endothelin-1 Neuropeptide Y, TNF, PDGF, FGF and so on.

The following examples illustrate specific, non-limiting experiments, or compound profiling operations, in accordance with the present invention.

EXAMPLE 1

TE-671 cells, human medulloblastoma (ATCC CRL 8805), naturally express endothelin subtype A receptor $ET_AR$. This receptor belongs to the family of seven transmembrane-spaning G-protein coupled receptors and is known to activate calcium mobilization in the cell cytoplasm upon binding to its specific agonist endothelin-1, a 21-amino acid peptide. To characterize the affinity of the agonist for the receptor, conventional methods measure the physiological response of the cell in the presence of several concentrations of the agonist or antagonist (Sakamoto, A. et al., 1994, incorporated herein by reference).

FIG. 9 illustrates a measurement of the activation of intracellular calcium mobilization ($Ca^{2+}$ measured in nanomolar concentration) as a function of the concentration of endothelin-1 (ET-1, measured in picomolar concentration), using the apparatus and method of the present invention. The apparatus was a negative pressure computer controlled unit as described above. This run was performed in the presence of several concentrations of $ET_AR$ specific competitive antagonist BQ-123 (shown in nanomolar concentration).

TE-671 cells were prepared for use in the cell physiometer of the present invention by growing them in a T75 flask until confluence. The growth media was decanted and the cells were washed twice with Dulbecco's phosphate buffered saline (DPBS) and supplemented with a fresh DPBS containing 2 ILM FURA-2$\mu$M, which easily penetrates into cell cytoplasm and is hydrolyzed there with nonspecific esterases to form FURA 2, a dye which is sensitive to the ionized form of calcium. After 30 min incubation, the cells were supplemented with the equal volume of fresh DPBS and incubated for further 30 min. The cells, now loaded with the dye, were detached from the flask bottom with 0.05% Trypsin-EDTA solution. The cells were then washed twice with DPBS, containing 0.1% soybean trypsin inhibitor, and resuspended in calcium-free, magnesium-free and phenol red-free Dulbecco's modified Eagle's medium (DMEM).

Briefly, with reference to FIG. 3, after calibration with minimum and maximum standards (339, 337), ET-1 solution, an agonistic test compound, was mixed with DPBS buffer in continuously changing proportion by the proportioning valve 311 and was directed through the proportioning valve 311, mixing chamber 331, diverting valve 333, and priming valve 341 into the mixing chamber 343, where it was mixed with a suspension of TE-671 cells to provide a final concentration of cells $4\times10^5$ cells/ml. At the same time, BQ-123, as a standard antagonist solution, was also directed to the mixing chamber 331 at a predetermined concentration prepared by mixing BQ-123 with DPBS in the proportioning valve 327, in a ratio of 1:1 with the ET-1 solution. In mixing chamber 343, the mixed flow of BQ-123 at constant concentration, and ET-1 at a continuously changing in time concentration is mixed with cells 349 in a ration of 2:1. This gives three fold final dilution for each component of the flow passing through mixing chamber 343 and eventually, detector 355. The proportioning valve 327, was programmed for the first, second and third runs to give final BQ-123 concentration of zero, 10 nM and 40 nM, respectively. The proportioning valve 311 was preprogrammed to give a final concentration of ET-1 in each run from 0 to 100 pM. Changes in intracellular calcium ion concentration in the TE-671 cells passing through the detector 315, were measured in real time as a function of ET-1 concentration using fluorescent dye FURA-2 as described above..

The flow rate and the length of the reaction developing line were chosen so that the time interval from the point of mixing the cells with the compound to the point of signal detection in the flow-through optical cell was 40 seconds. The time required for the complete concentration gradient run to generate the curves in FIG. 9 was five minutes using the present invention. In contrast, in a conventional assay using the phosphatidylinositol turnover rate as an indicator of $ET_AR$ stimulation, it usually takes several hours to get only a few concentration points on the response curve, and it would take an inordinate amount of time to generate a complete curve as shown in FIG. 9.

FIG. 10 is a logarithmic transformation of the data in FIG. 9, which is used in the art to calculate maximal cell response in the presence of antagonist as well as $EC_{50}$ value for agonist and $pA_2$ value for antagonist. The $EC_{50}$ value calculated from the activation curve without BQ-123 is equal to 10 pM and one can see that the activation curves in FIG. 10 are parallel shifted to the right in the presence of BQ-123, which is known in the art as characteristic for competitive type of inhibition. The average $pA_2$ value calculated from the two different concentrations of BQ-123 is equal to 7.96. This corresponds to inhibition constant, $K_1$, for BQ-123 of 11 nM. The $EC_{50}$ and $pA_2$ values are in close agreement with the literature data (Masaki Ihara et al., 1992, is incorporated herein by reference).

EXAMPLE 2

Figure 11:
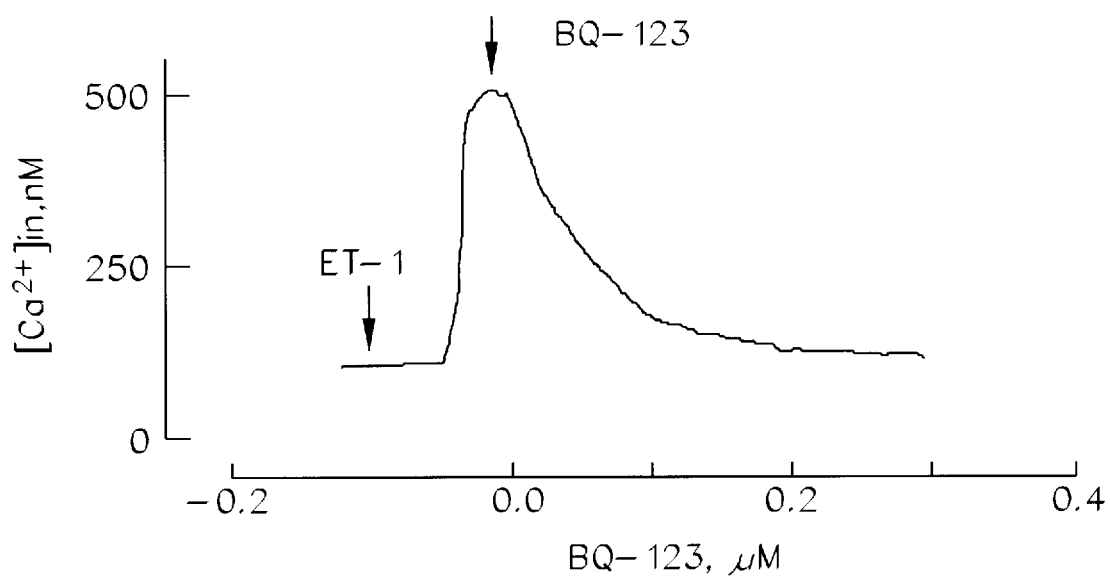
FIG. 11 represents the experimental results of ET-1 dose dependent $Ca^{2+}$ mobilization in TE-671 cells with the subsequent inhibition with the BQ-123

FIG. 11 illustrates the inhibition of ET-1 induced intracellular calcium mobilization with BQ-123 in TE-671 cells. The same cell physiometer apparatus and cell preparation procedure was used here as in Example 1.

In this experiment, ET-1 was introduced at a constant concentration from the "standard" sipper nozzle of the inventive apparatus and BQ-123 was introduced through the "compound" nozzle of the apparatus. In this example, as in Example 1, the concentration run was five minutes and the reaction time (from mixing to detection) was forty seconds.

Briefly, with reference to FIG. 3, after calibration with minimum and maximum standards (337, 339), ET-1 solution, an agonist standard solution, was directed at a predetermined concentration prepared by proportioning valve 327 by mixing it with DPBS buffer, through priming valve 329, mixing chamber 331, diverting valve 333 and priming valve 341 and then into mixing chamber 343, where it was mixed with a suspension of TE-671 cells to provide a final concentration of cells of $4\times10^5$ cells/ml. At the same time, DPB in volumetric ratio of 1:1 to ET-1 solution was directed through intake port 309 and outlet port 312 of proportioning valve 311, priming valve 313 to mixing chamber 331 and further through fluidics system to the detector 355. After the intracellular calcium concentration in the presence of the standard agonist is stabilized, BQ-123, as an antagonistic test compound, was directed from intake port 307 of proportioning valve 311, instead of DPBS, to the mixing chamber 331 at continuously changing concentrations prepared by mixing BQ-123 with DPBS in proportioning valve 311, through the system in a volumetric ratio of 1:1 with the ET-1 solution. In mixing chamber 343, the mixed flow of ET-1 at constant concentration, and BQ-123 at a continuously changing in time concentration was mixed with cells 349 in a ratio of 2:1. This gives three fold final dilution for each component of the flow passing through mixing chamber 343 and, eventually, detector 355. The proportioning valve 327 was preprogrammed to give a final concentration of ET-1 of 40 pM at the detector. The proportioning valve 311 was preprogrammed to give final concentration of BQ-123 from 0 to 300 nM. Changes in intracellular calcium ion concentration in the TE-6712 cells passing through the detector 355, were measured in real time as a function of BQ-123 concentration using fluorescent dye FURA-2 as described above.

EXAMPLE 3

Figure 12:
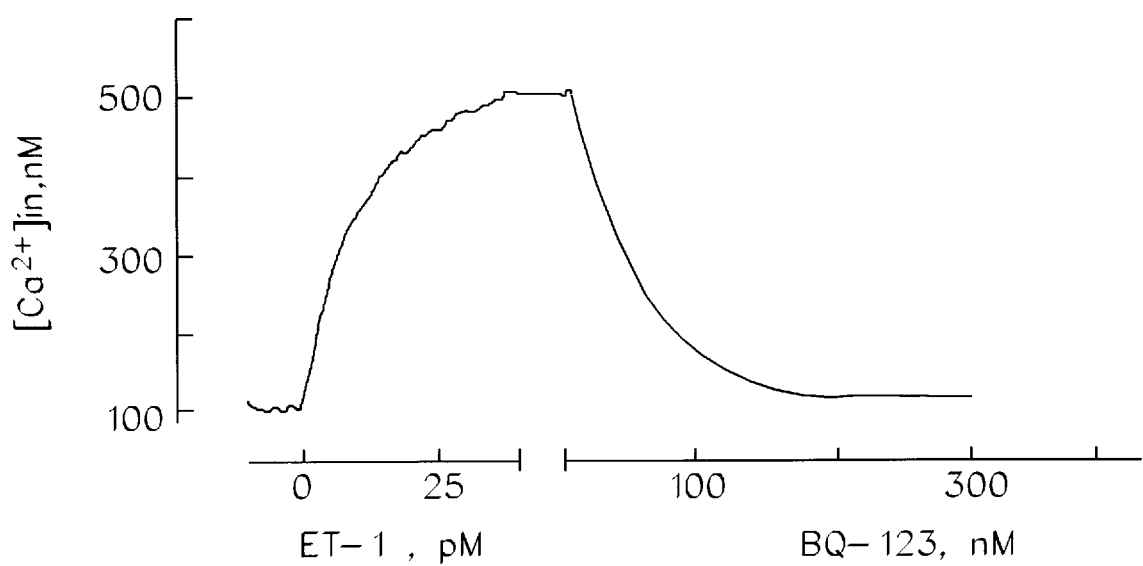
FIG. 12 illustrates the "null method" experimental results of ET-1 dose dependent $Ca^{2+}$ mobilization in TE-671 cells with subsequent inhibition with BQ-123.

FIG. 12 shows the "null method" experiment design (Lazareno & Birdsall, 1993, incorporated herein by reference). This example uses the same instrument and the same reagents as in Examples 1 and 2.

In this example, a first concentration gradient of ET-1 coming from the "standard" nozzle 323 of the inventive apparatus is prepared with the buffer solution coming from the "compound" nozzle. When the final ET-1 concentration has reached the value of 40 pM, the gradient device 1 keeps the ET-1 concentration constant and gradient device 2 starts raising the concentration of the BQ-123 coming from the "compound" nozzle. One can switch the agonist gradient over to an antagonist at any predetermined concentration of the agonist.

Although the invention has been described in detail with reference to certain particular embodiments thereof, it will be understood that any variations and modifications apparent to those of skill in the art will still fall within the spirit and scope of the invention. Other embodiments not specifically described herein may fall within the spirit and scope of the present invention as provided by the following claims.

What is claimed is:

1. An apparatus for automatically measuring the effect of a plurality of test compounds on living cells, comprising:

a test compound sampler for sequentially and automatically providing samples of multiple test compounds;

a cell suspension source for providing a suspension of living cells;

a mixing chamber, coupled to the test compound sampler and the cell suspension source, for receiving the samples of the test compounds from the test compound sampler, receiving the suspension of living cells from the cell suspension source, and for mixing each test compound with the suspension of living cells so as to provide a respective test solution for each test compound;

a detector, coupled to the mixing chamber, for receiving each respective test solution and for measuring a cellular response of the suspended cells for each said test solution; and a conduit establishing a flow channel between the mixing chamber and the detector, such that each said test solution flows from the mixing chamber to the detector.

2. The apparatus of claim 1 further comprising a standard compound sampler, coupled to said mixing chamber, for providing a sample of a standard compound having a known effect on said cellular response of said suspended cells, wherein said mixing chamber receives the sample of the standard compound from the standard compound sampler and mixes the standard compound with the suspended cells and said detector measures the cellular response of the suspended cells to the standard compound.

3. The apparatus of claim 2 wherein said mixing chamber simultaneously mixes said test compound and said standard compound with said suspended cells and said detector detects said known effect or an alteration of said known effect.

4. The apparatus of claim 2 further comprising:
a first gradient device, coupled to said test compound sampler, for automatically adjusting the concentration level of said test compound transferred to said mixing chamber from said test compound sampler; and
a second gradient device, coupled to said standard compound sampler, for automatically adjusting the concentration level of said standard compound transferred to said mixing chamber from said standard compound sampler.

5. The apparatus of claim 4 further comprising a switching valve, coupled to the first and second gradient devices at an input of the switching valve and coupled to said mixing chamber at an output of the switching valve, for selectively switching the flow of a concentration of said test compound or a concentration of said standard compound or both to the mixing chamber where the test compound and/or the standard compound is then mixed with said suspension of cells.

6. The apparatus of claim 5 further comprising a calibration unit, coupled to said switching valve, wherein the switching valve also selectively switches the flow of a calibration solution provided by the calibration unit into said mixing chamber where the calibration solution is mixed with said suspension of cells.

7. The apparatus of claim 6 wherein said conduit comprises a reaction developing line coupled to the output of said mixing chamber, for receiving a mixture of said cell suspension mixed with either said test compound, said standard compound or said calibration solution, and providing a flow path for the mixture such that there is adequate time for the suspension cells to react with the test compound, the standard compound or the calibration solution, wherein the reaction developing line is further coupled to the input of said detector which receives the mixture from the reaction developing line.

8. The apparatus of claim 7 wherein said detector detects changes in intracellular ion concentration.

9. The apparatus of claim 8 wherein said ion is calcium, magnesium, proton, sodium, or potassium.

10. The apparatus of claim 8 wherein said detector detects changes in intracellular ion concentration using an intracellular dye.

11. The apparatus of claim 10 wherein said dye is fluorescent.

12. The apparatus of claim 7 further comprising:
a controller, coupled to said first and second gradient devices, said test compound sampler, said standard compound sampler and said switching valve, for controlling their operation; and
a computer, coupled to the controller, for sending command signals to the controller in accordance with a software program implemented by the computer, wherein the computer is also coupled to said detector in order to send and receive cell response measurement signals to and from the detector.

13. The apparatus of claim 1 wherein said test compound sampler is an automated robotic sampler capable of selecting a specified test compound from a library of test compounds.

14. The apparatus of claim 13 further comprising:
a controller, coupled to said test compound sampler, for controlling the operation of the test compound sampler; and
a computer, coupled to the controller, for sending command signals to the controller in accordance with a software program implemented by the computer, thereby controlling the selection and retrieval of test compounds by the test compound sampler from said test compound library.

15. The apparatus of claim 14 further comprising a gradient pump having an input and an output, coupled to said test compound sampler, for adjusting the concentration level of said test compound transferred to said mixing chamber from said test compound sampler, wherein:
said test compound sampler comprises:
a first intake nozzle for receiving said specified test compound;
a second intake nozzle for receiving a buffer solution; and
wherein said gradient pump is coupled to the first and second intake nozzles and receives specified concentrations of the test compound by adjusting the amount of test compound and buffer solution received by the first and second intake nozzles, respectively, wherein the buffer solution is a diluting agent of the test compound.

16. The apparatus of claim 15 further comprising a standard compound sampler for providing a sample of a standard compound to said mixing chamber.

17. The apparatus of claim 16 wherein said standard compound sampler is an automated robotic sampler capable of selecting a specified standard compound from a library of standard compounds.

18. The apparatus of claim 17 further comprising a second gradient pump having an input and an output, coupled to said standard compound sampler, for adjusting the concentration level of said standard compound provided to said mixing chamber from said standard compound sampler, wherein:
said standard compound sampler comprises:
a third intake nozzle for receiving said specified standard compound;
a fourth intake nozzle for receiving a buffer solution; and
wherein said second gradient pump is coupled to the third and fourth intake nozzles and receives specified concentrations of the standard compound by adjusting the amount of standard compound and buffer solution received by the third and fourth intake nozzles, respectively, wherein the buffer solution is a diluting agent of the standard compound.

19. The apparatus of claim 18 further comprising a second mixing chamber coupled to the outputs of the first and second gradient pumps, for receiving and mixing said specified concentrations of said specified test compound and said specified standard compound, such that the output of the second mixing chamber is provided to said first mixing chamber.

20. The apparatus of claim 19 further comprising:
a calibration unit for providing a calibration solution; and
a switching valve, having a first input coupled to said second mixing chamber, a second input coupled to the calibration unit, and an output coupled to said first mixing chamber, for switching between the flow of either a compound mixture from the second mixing chamber or the calibration solution from the calibration unit and then providing the flow to the first mixing chamber where it may be mixed with said cell suspension.

21. The apparatus of claim 20 wherein said calibration unit comprises:
a calibration maximum solution which provides for maximal cell response when mixed with said cell suspension;
a calibration minimum solution which provides for minimal cell response when mixed with said cell suspension;
a diverting valve having a first input coupled to the calibration maximum solution and a second input coupled to the calibration minimum solution, for switching between the flow of either the calibration maximum solution or calibration minimum solution; and
a pump, coupled to the output of the diverting valve and an input of said switching valve, for pumping either the calibration maximum or calibration minimum solution from the diverting valve into the switching valve.

22. The apparatus of claim 21 further comprising a second pump, coupled to an input of said first mixing chamber, for pumping said suspension of cells from said cell suspension input into the first mixing chamber.

23. The apparatus of claim 22 wherein said conduit comprises a reaction developing line, having an input coupled to an output of said first mixing chamber and a output coupled to an input of said detector, for providing a flow path and a reaction time delay for a mixture received from the first mixing chamber and for providing the mixture to the detector.

24. The apparatus of claim 23 further comprising:
a controller, coupled to said first and second gradient pumps, said test compound sampler, said standard compound sampler and said switching valve, said first and second mixing chambers, said first and second pumps and said diverting valve for controlrmg their operation; and
a computer, coupled to the controller, for sending command signals to the controller in accordance with a software program implemented by the computer, wherein the computer is also coupled to said detector in order to send and receive cell response measurement signals to and from the detector.

25. The apparatus of claim 24 wherein said detector detects changes in intracellular ion concentration.

26. The apparatus of claim 25 wherein said ion is calcium, magnesium, proton, sodium, or potassium.

27. The apparatus of claim 25 wherein said detector detects changes in intracellular ion concentration using an intracellular dye.

28. The apparatus of claim 27 wherein said dye is fluorescent.

29. The apparatus of claim 13 further comprising:
a pump, coupled to the output of said detector, for providing negative pressure to the apparatus;
a proportionating valve, coupled to said test compound sampler, for adjusting the concentration level of said test compound transferred to said mixing chamber from said test compound sampler, wherein said test compound sampler further comprises:
a first intake nozzle for receiving said specified test compound;
a second intake nozzle for receiving a buffer solution; and
the proportionating valve receives specified concentrations of the test compound by adjusting the amount of test compound and buffer solution received by the first and second intake nozzles, respectively, wherein the buffer solution is a diluting agent of the test compound.

30. The apparatus of claim 29 further comprising:
an automated standard compound sampler capable of selecting a specified standard compound from a library of standard compounds, said standard compound sampler including a third intake nozzle for receiving said specified standard compound and a fourth intake nozzle for receiving a buffer solution; and
a second proportionating valve, coupled to the third and fourth intake nozzles, for receiving specified concentrations of the standard compound by adjusting the amount of standard compound and buffer solution received by the third and fourth intake nozzles, respectively, wherein the buffer solution is a diluting agent of the standard compound.

31. The apparatus of claim 30 further comprising:
a first priming valve, coupled to the output of said first proportionating valve, for receiving said specified concentration of said test compound and providing the test compound to said mixing chamber;
a second priming valve, coupled to the output of said second proportionating valve, for receiving said specified concentration of said standard compound and providing the standard compound to the mixing chamber.

32. The apparatus of claim 31 further comprising:
a calibration unit including a calibration maximum solution which provides for maximal cell response when mixed with said cell suspension and a calibration minimum solution which provides for minimal cell response when mixed with the cell suspension;
a first diverting valve, having a first input coupled to the calibration maximum solution and a second input coupled to the calibration minimum solution, for switching between the flow of either the calibration maximum solution or calibration minimum solution;
a second diverting valve, having a first input coupled to the output of said mixing chamber and a second input coupled to the output of said first diverting valve, for switching between the flow of either a calibration solution from the first diverting valve or a mixture from the mixing chamber;
a third priming valve, coupled to the output of the second diverting valve, for receiving a mixture from the second diverting valve; and
a second mixing chamber, coupled to the output of the third priming valve, for mixing a mixture provided by the third priming valve with said cell suspension, wherein said cell suspension input and said detector are coupled to the second mixing chamber instead of the first mixing chamber.

33. The apparatus of claim 32 wherein said conduit comprises a reaction developing line, having an input coupled to the output of said second mixing chamber and an output coupled to an input of said detector, for providing a flow path and a reaction time delay for a mixture received from the second mixing chamber before the mixture reaches said detector.

34. The apparatus of claim 33 wherein said cell suspension input comprises:
a cell suspension reservoir;
a buffer reservoir;
a third diverting valve, having a first input coupled to the cell suspension reservoir and a second input coupled to the buffer reservoir, for adjusting the concentration of the cell suspension, wherein the buffer is a diluting agent of the cell suspension; and
a fourth priming valve, coupled to the output of the third diverting valve, for receiving the cell suspension mixture from the third diverting valve and providing this mixture to said second mixing chamber.

35. The apparatus of claim 34 wherein said detector detects changes in intracellular ion concentration.

36. The apparatus of claim 35 wherein said ion is calcium, magnesium, proton, sodium, or potassium.

37. The apparatus of claim 34 wherein said detector detects changes in intracellular ion concentration using an intracellular dye.

38. The apparatus of claim 37 wherein said dye is fluorescent.

39. An apparatus for measuring the effect of a test compound on living cells, comprising:
a test compound source;
a cell suspension reservoir providing a suspension of living cells;
a first channel, coupled to the test compound source, through which the test compound can flow;
a second channel, coupled to the cell suspension source, through which the suspension of living cells can flow;
a mixing zone, coupled to the first and second channels, so that the test compound and cell suspension can flow into the mixing zone to provide a desired mixture of the test compound and the cell suspension in said mixing zone;
a fluid flow path through which said mixture can flow from the mixing zone; and
a detector, coupled to the fluid flow path, which measures a cellular response of the suspended cells to the test compound, wherein the desired mixture of the test compound and the cell suspension flows along the fluid flow path from the mixing chamber to the detector.

40. The apparatus of claim 39 further comprising:
a diluent source for providing a diluting agent of the test compound;
a third channel, coupled to the diluent source, through which the diluting agent can flow; and
wherein said mixing zone is coupled to the third channel, to receive the diluting agent so as to provide a desired concentration of said test compound.

41. The apparatus of claim 40 further comprising:
a standard compound source, providing a standard compound having a known effect on said suspension of cells; and a fourth channel, coupled to the standard compound source, through which the standard compound can flow, wherein said mixing chamber is coupled to the fourth channel, receives the standard compound from the fourth channel, and mixes the standard compound with the suspension of cells; and
wherein said detector measures a cellular response of the suspended cells to the standard compound.

42. The apparatus of claim 41 wherein said mixing chamber simultaneously mixes said test compound and said standard compound with said suspended cells and said detector detects said known effect or an alteration of said known effect.

43. The apparatus of claim 42 further comprising a controller, coupled to the first, second, third and fourth channels, which automatically controls a flow of test compound, buffer solution, cell suspension and standard compound through the first, second, third and fourth channels, respectively.

44. The apparatus of claim 39 further comprising a controller, coupled to the first channel, which automatically controls a flow of the test compound through the first channel.

45. An apparatus for measuring the effect of a test compound on living cells, comprising:
a test compound source;
a first gradient device, coupled to the test compound source, for automatically adjusting the concentration level of a test compound transferred to said mixing chamber from said test compound source;
a cell suspension source;
a mixing chamber, coupled to the first gradient device and the cell suspension source, which receives the test compound and a suspension of living cells from the cell suspension source and mixes the test compound with the suspension of living cells; and
a detector, coupled to the mixing chamber, for measuring a cellular response of the suspended cells to the test compound.

46. The apparatus of claim 45 further comprising a standard compound source which provides a standard compound having a known effect on said suspension of cells, wherein said mixing chamber is coupled to the standard compound source, receives the standard compound, and mixes the standard compound with the suspension of cells, and wherein said detector measures a cellular response of the suspended cells to the standard compound.

47. The apparatus of claim 46 wherein said mixing chamber simultaneously mixes said test compound and said standard compound with said suspended cells and said detector detects said known effect or an alteration of said known effect.

48. The apparatus of claim 46 further comprising a second gradient device, coupled to said standard compound source, for automatically adjusting the concentration level of said standard compound transferred to said mixing chamber from said suspension of cells.

49. The apparatus of claim 48 further comprising a controller, coupled to the first and second gradient devices, for automatically controlling a flow of the test compound and automatically controlling a flow of the standard compound, into said mixing chamber.

50. The apparatus of claim 45 further comprising a controller, coupled to the first gradient device, for automatically controlling a flow of the test compound into said mixing chamber.

* * * * *